(12) United States Patent
Van Wyk

(10) Patent No.: US 10,745,699 B2
(45) Date of Patent: *Aug. 18, 2020

(54) ANTISENSE OLIGONUCLEOTIDES FOR THE TREATMENT OF USHER SYNDROME TYPE 2

(71) Applicant: STICHTING KATHOLIEKE UNIVERSITEIT, Nijmegen (NL)

(72) Inventor: Hendrikus Antonins Rudolfus Van Wyk, Nijmegen (NL)

(73) Assignee: STICHTING KATHOLIEKE UNIVERSITEIT, Nijmegen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/027,451

(22) Filed: Jul. 5, 2018

(65) Prior Publication Data

US 2019/0017048 A1    Jan. 17, 2019

Related U.S. Application Data

(63) Continuation of application No. 15/324,572, filed as application No. PCT/EP2015/065736 on Jul. 9, 2015, now Pat. No. 10,131,910.

(30) Foreign Application Priority Data

Jul. 10, 2014    (EP) .................................. 14176438

(51) Int. Cl.
    *C12N 15/113*      (2010.01)

(52) U.S. Cl.
    CPC ........ *C12N 15/113* (2013.01); *C12N 2310/11* (2013.01); *C12N 2310/315* (2013.01); *C12N 2310/321* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 5,139,941 A | 8/1992 | Muzyczka | |
| 6,531,456 B1 | 3/2003 | Kurtzman | |
| 6,875,736 B2 | 4/2005 | Rana | |
| 7,592,443 B2 | 9/2009 | Khvorova | |
| 10,131,910 B2 * | 11/2018 | Van Wyk | C12N 15/113 |
| 2001/0053519 A1 | 12/2001 | Fodor | |
| 2005/0106731 A1 | 5/2005 | Davidson | |
| 2013/0129668 A1 | 5/2013 | Firestein | |

FOREIGN PATENT DOCUMENTS

| | | |
|---|---|---|
| EP | 1619249 | 1/2006 |
| EP | 2425814 | 3/2012 |
| WO | 200125486 A1 | 4/2001 |
| WO | WO 2002024906 | 3/2002 |
| WO | 2012151324 A1 | 11/2012 |
| WO | 2014022739 A2 | 2/2014 |
| WO | WO-2015134812 A1 * | 9/2015 |

OTHER PUBLICATIONS

International Search Report for PCT/EP2015/065736.
Gorman et al., "Stable alteration of pre-mRNA splicing patterns by modified U7 small nuclear RNAs"; XP-002642571 (Apr. 1998); Proc. Natl. Acad. Sci. USA; vol. 95; Biochemistry; pp. 4929-4934.
Lenassi et al., "The effect of the common c.2299delG mutation in USH2A on RNA Splicing"; Elsevier (2014); Experimental Eye Research; 122: pp. 9-12.
McGee et al., "Novel mutations in the long isoform of the USH2A gene in patients with Usher syndrome type II or non-syndromic retinitis pigmentosa"; NIH Public Access (Jul. 2010); J. Med. Genet.; 47(7): pp. 499-506.
Mitrpant et al., "Improved Antisense Oligonucleotide Design to Suppress Aberrant SMN2 Gene Transcript Processing: Towards a Treatment for Spinal Muscular Atrophy"; XP-002733112 (Apr. 2013); PLOS One; Public Library of Science; vol. 8; Issue 4; e62114.
Vaché et al., "Usher syndrome type 2 caused by activation of an USH2A pseudoexon: implications for diagnosis and therapy"; Wiley Periodicals, Inc.; Human Genome Variation Society (2011); vol. 33 (1); pp. 104-108.
Van Wijk, et al., "Identification of 51 novel exons of the Usher syndrome type 2A (USH2A) gene that encode multiple conserved functional domains and that are mutated in patients with Usher syndrome type II"; Am. J. Hum. Genet. (2004); 74: pp. 738-744.
XP002744859; Sequence 63854 from Patent WO2012149438; retrieved from EBI accession No. EM_PAT:JA980903; Database accession No. JA980903 sequence.
XP-002744860; Sequence 47894 from Patent WO2012149438; retrieved from EBI accession No. EM PAT:JA964943; Database accession No. JA964943 sequence.
Random Primer 24, sold by New England Biolabs (see p. 121 of the 1998/99 New England Biolabs Catalog). (Year 1998).
Aartsma-Rus et al, "Exonic sequences provide better targets for antisense oligonucleotides than splice site sequences in the modulation of Duchenne muscular dystrophy splicing," Oligonucleotides, 2010, 20:69-77.
Aartsma-Rus et al, "Guidelines for Antisense Oligonucleotide Design and Insight Into Splice-modulating Mechanisms," Mol. Ther., 2008, 17(3):548-533.
Bainbridge et al, "Effect of gene therapy on visual function in Leber's congenital amaurosis," N Engl J Med, 2008, 358:2231-2239.
Baux et al, "Enrichment of LOVD-USHbases with 152 USH2A genotypes defines an extensive mutational spectrum and highlights missense hotspots," Hum. Mutat., 2014, 35:1179-1186.
Baux et al, "Molecular and in silico analyses of the full-length isoform of usherin identify new pathogenic alleles in Usher type II patients," Hum. Mutat., 2007, 28(8):781-789.

(Continued)

*Primary Examiner* — J. E Angell
(74) *Attorney, Agent, or Firm* — Fish & Richardson P.C.

(57) ABSTRACT

The invention relates to the fields of medicine and immunology. In particular, it relates to novel antisense oligonucleotides that may be used in the treatment, prevention and/or delay of Usher syndrome type 2A and/or USH2A-associated non syndromic retina degeneration.

24 Claims, 9 Drawing Sheets

Specification includes a Sequence Listing.

(56) References Cited

OTHER PUBLICATIONS

Chiorini, et al., "Cloning and characterization of adeno-associated virus type 5," J. Virol., 1999, 73:1309-1319.
Cideciyan et al, "Human gene therapy for RPE65 isomerase deficiency activates the retinoid cycle of vision but with slow rod kinetics," Proc Natl. Acad. Sci. USA, 2008, 105:15112-15117.
Cirak et al, "Exon skipping and dystrophin restoration in patients with Duchenne muscular dystrophy after systemic phosphorodiamidate morpholino oligomer treatment: an open-label, phase 2, doseescalation study," Lancet, 2011, 378(9791):595-605.
Cirak et al, Restoration of the Dystrophin-associated Glycoprotein Complex After Exon Skipping Therapy in Duchenne Muscular Dystrophy, Mol. Ther., 2012, 20(2):462-467.
Colella et al, "Efficient gene delivery to the coneenriched pig retina by dual AAV vectors," Gene. Ther., 2014, 21:4:450-456.
Dorn and Kippenberger, "Clinical application of CpG-, non-CpG-, and antisense oligodeoxynucleotides as immunomodulators," Curr Opin Mol Ther, 2008, 10(1) 10-20.
Dreyer et al, "Spectrum of USH2A mutations in Scandinavian patients with Usher syndrome type II," Hum. Mutat., 2008, 29(3):451, 15 pages.
Egholm et al, "PNA hybridizes to complementary oligonucleotides obeying the Watson-Crick hydrogenbonding rules," Nature, 365:566-568.
Friesen & Darby, "Specific RNA binding proteins constructed from zinc fingers," Nature Structural Biology, 1998, 5:543-546.
Gamundi et al, "Transcriptional expression of cisacting and transacting splicing mutations cause autosomal dominant retinitis pigmentosa," Hum. Mutat., 2008, 29(6):869-878.
Garcia-Garcia et al, "Mutational screening of the USH2A gene in Spanish USH patients reveals 23 novel pathogenic mutations," Orphanet J. Rare. Dis., 2011, 6:65, 13 pages.
Goemans et al, "Systemic administration of PRO051 in Duchenne's muscular dystrophy," N.Engl.J.Med., 2011, 364(16):1513-1522.
Govindaraju & Kumar, "Backbone-extended pyrrolidine peptide nucleic acids (bepPNA): design, synthesis and DNA/RNA binding studies," Chem. Commun, 2005, 495-497.
Hartong et al, "Retinitis pigmentosa," Lancet, 2006, 368(9549): 1795-1809.
Hashimoto et al, "Lentiviral gene replacement therapy of retinas in a mouse model for Usher syndrome type 1B," Geme. Ther., 2007, 14(7):584-594.
Hauswirth et al, "Treatment of Leber Congenital Amaurosis Due to RPE65 Mutations by Ocular Subretinal Injection of Adeno-Associated Virus Gene Vector: Short-Term Results of a Phase I Trial," Hum. Gene. Ther., 2008, 979-990.
Kimberling et al, "Frequency of Usher syndrome in two pediatric populations: implications for genetic screening of deaf and hard of hearing children," Genet Med, 2010, 12:512-516.
Lentz et al., "Rescue of hearing and vestibular function in a mouse model of human deafness," Nat Med., 2013, 19(3):345-50.
Lopes et al, "Retinal gene therapy with a large MYO7A cDNA using adenoassociated virus," Gene. Ther., 2013, 20(8):824-833.
Maguire et al, "Safety and efficacy of gene transfer for Leber's congenital amaurosis," N. Engl. J. Med., 2008, 358:2240-2248.
Morita et al, "2'-O,4'-C-Ethylene-bridged nucleic acids (ENA) with nucleaseresistance and high affnity for RNA," Nucleic Acid Res Supplement, 2001, 1:241-242.
Nielsen et al, "Sequence-Selective Recognition of DNA by Strand Displacement with a Thymine-Substituted Polyamide," Science, 1991, 254:1497-1500.
Scaffidi et al, "Reversal of the cellular phenotype in the premature aging disease Hutchinson-Gilford progeria syndrome," Nat. Med., 2005, 11(4):440-445.
Smith et al, "An increased specificity score matrix for the prediction of SF2/ASF specific exonic splicing enhancers," Hum. Mol. Genet., 2006, 15:2490-2508.
Stabej, et al, "Comprehensive sequence analysis of nine Usher syndrome genes in the UK National Collaborative Usher Study," J. Med. Genet., 2012, 49(1):27-36.
Suter et al, "Double-target antisense U7 snRNAs promote efficient skipping of an aberrant exon in three human beta thalassemic mutations," Hum Mol Genet, 1999, 8(13):2415-23.
Zallocchi et al, "EIAV-based retinal gene therapy in the shaker1 mouse model for usher syndrome type 1B: development of UshStat," Plos One, 2014, 9(4):e94272.

\* cited by examiner

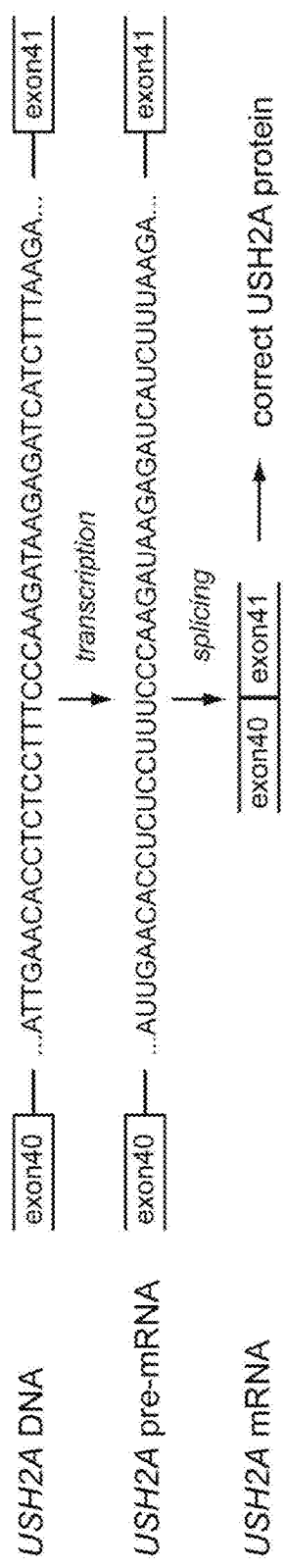
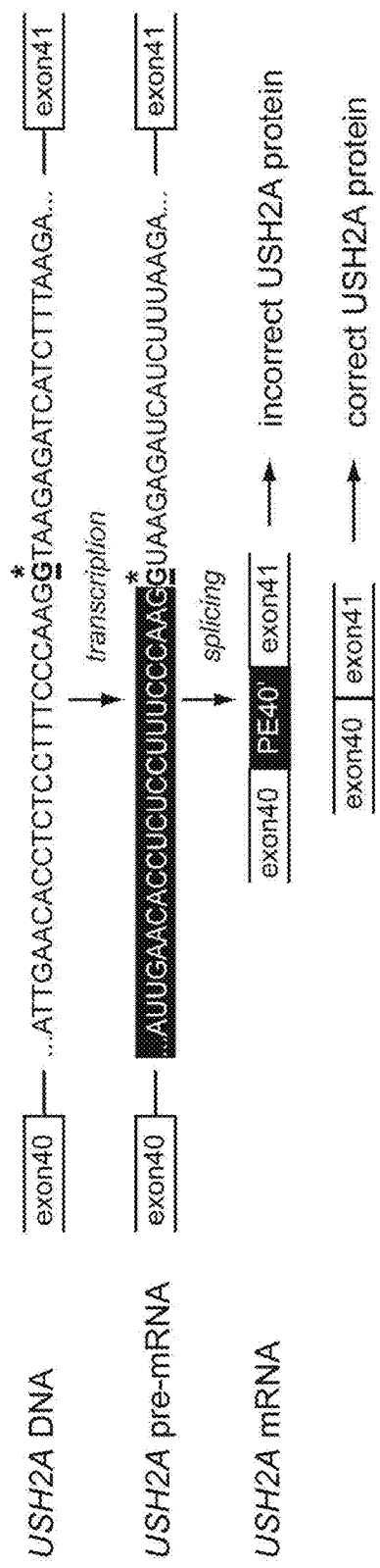

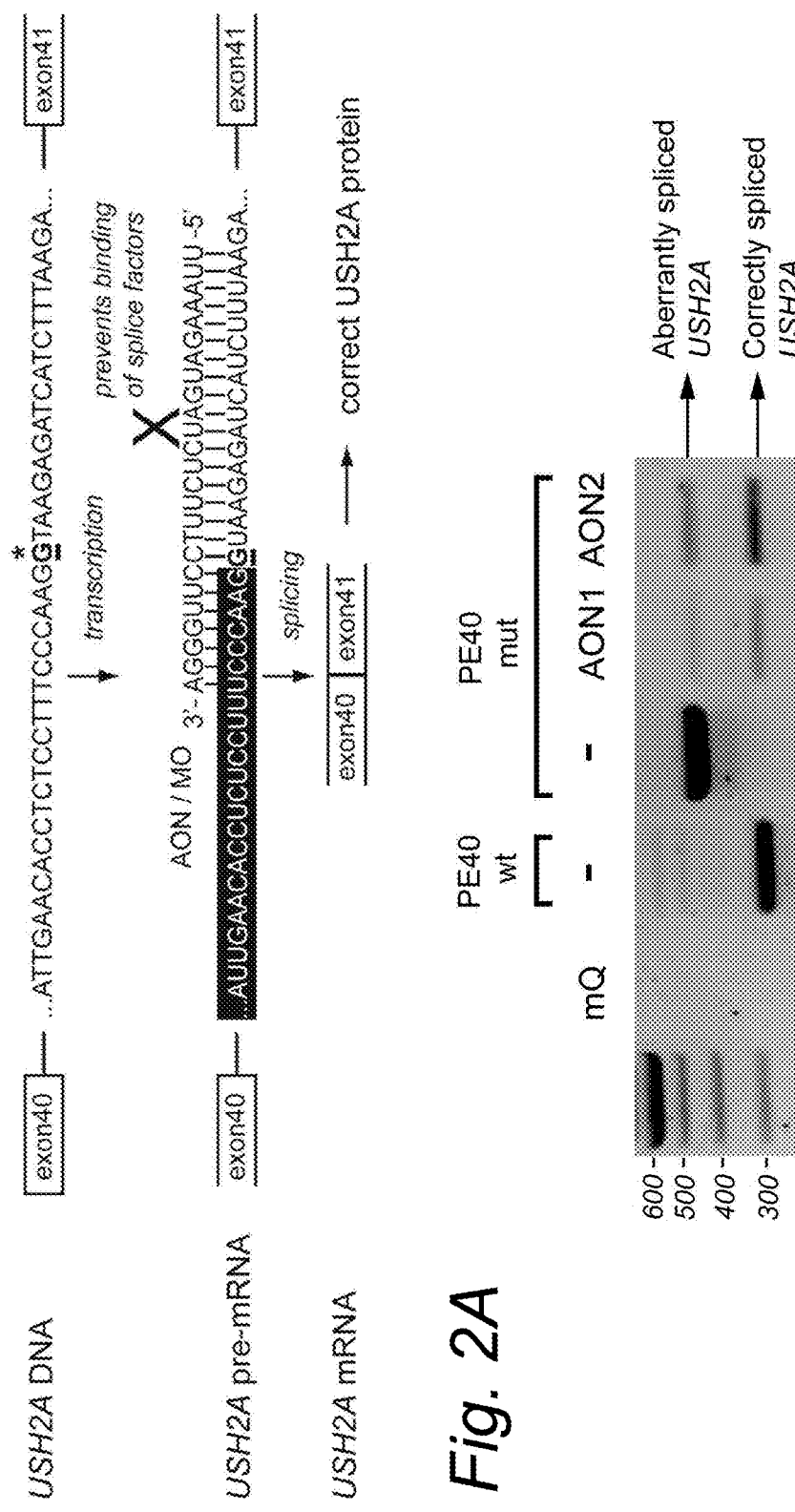

pCI-neo-RHO ex3-5_USH2A exon13 splice construct pCI-neo-RHO ex3-5_USH2A exon50 splice construct

ANTISENSE OLIGONUCLEOTIDES FOR THE TREATMENT OF USHER SYNDROME TYPE 2

CROSS REFERENCE TO RELATED APPLICATIONS

This application is a continuation of U.S. patent application Ser. No. 15/324,572, filed Jan. 6, 2017, as a 35 U.S.C. § 371 national phase application of PCT/EP2015/065736, which was filed Jul. 9, 2015, and claimed the benefit of European patent application No. 14176438.1, filed Jul. 10, 2014, all of which are incorporated herein by reference as if fully set forth.

The sequence listing filed with this application, titled "Sequence Listing," having a file size of 2,289,879 bytes, and created Jul. 3, 2018 is incorporated herein by reference as if fully set forth.

FIELD OF THE INVENTION

The invention relates to the fields of medicine and immunology. In particular, it relates to novel antisense oligonucleotides that may be used in the treatment, prevention and/or delay of Usher syndrome type 2A and/or USH2A-associated non syndromic retina degeneration.

BACKGROUND OF THE INVENTION

Usher syndrome (USH) and non-syndromic retinitis pigmentosa (NSRP) are degenerative diseases of the retina. USH is clinically and genetically heterogeneous and by far the most common type of inherited deaf-blindness in man (1 in 6,000 individuals) (Kimberling et al, 2010). The hearing impairment in USH patients is mostly stable and congenital and can be partly compensated by hearing aids or cochlear implants. NSRP is more prevalent than USH, occurring in 1 per 4,000 individuals (Hartong et al, 2006). The degeneration of photoreceptor cells in USH and NSRP is progressive and often leads to complete blindness between the third and fourth decade of life, thereby leaving time for therapeutic intervention. Mutations in the USH2A gene are the most frequent cause of USH explaining up to 50% of all USH patients worldwide (±1300 patients in The Netherlands) and, as indicated by McGee et al (2010), also the most prevalent cause of NSRP in the USA (likely accounting for 12-25% of all cases of retinitis pigmentosa (RP); ±600 patients in The Netherlands). They are spread throughout the 72 USH2A exons and their flanking intronic sequences, and consist of nonsense and missense mutations, deletions, duplications, large rearrangements, and splicing variants (USHbases and unpublished results). The by far most frequently mutated exon is exon 13, which contains two founder mutations (c.2299delG (p.E767SfsX21) in USH2 patients and c.2276G>T (p.C759F) in NSRP patients). For exon 50, fifteen pathogenic mutations have been reported, of which at least eight are clearly protein truncating (Baux et al, 2007 & 2014; Garcia-Garcia et al, 2011; Dreyer et al, 2008; McGee et al, 2010; Le Quesne Stabej et al, 2012). Recently the first deep-intronic mutation in intron 40 of USH2A (c.7595-2144A>G) was reported (Vaché et al, 2012). This mutation creates a cryptic high-quality splice donor site in intron 40 resulting in the inclusion of an aberrant exon of 152 bp in the mutant USH2A mRNA, and inserts a premature stop codon in exon 41 when translated (FIGS. 1A and B). USH and other retinal dystrophies, for long have been considered as uncurable disorders. Recent and ongoing phase I/II clinical trials using gene augmentation therapy have led to promising results in selected groups of LCA/RP/USH patients with mutations in the RPE65 (Bainbridge et al, 2008; Cideciyan et al, 2008; Hauswirth et al, 2008; Maguire et al, 2008) and MYO7A (Hashimoto et al, 2007; Lopes et al, 2013; Colella et al, 2014; Zallocchi et al, 2014) genes. The size of the coding sequence (15,606 bp) and alternative splicing of the USH2A gene and mRNA, respectively, hamper gene augmentation therapy, due to the currently limiting cargo size of many available vectors (e.g. adeno-associated (AAV) and lentiviral vectors). Despite the broad clinical potential of antisense oligonucleotide (AON)-based therapy, it is not frequently used in the vertebrate eye. AONs are small (16-25 nucleotide) polynucleotide molecules that are able to interfere with splicing as their sequence is complementary to that of target pre-mRNA molecules. Upon binding of an AON, the targeted region of the pre-mRNA is no longer available for splicing factors which results in skipping of the exon that is targeted by the AON. Therapeutically, this methodology can be used in two ways: a) to redirect normal splicing of genes in which mutations activate cryptic splice sites and b) to skip exons that carry (protein-truncating) mutations in such a way, that the reading frame of the mRNA remains intact and a (partially) functional protein is made. For the USH2A gene 28 out of the 72 described exons can potentially be skipped without disturbing the overall reading frame of the transcript. Both methods are already successfully applied in patients with severe genetic disorders (Scaffidi et al, 2005; Cirak et al, 2011a/b; Goemans et al, 2011). It is therefore an objective of the invention to provide a convenient therapeutic strategy for the prevention, treatment or delay of USH and/or NSRP caused by mutations in exons 13, 50 and intron 40 of USH2A. To date however, treatment options available for Usher syndrome patients are limited to ear implants or hearing aids. No treatment for Usher syndrome related blindness is currently available.

BRIEF DESCRIPTION OF THE DRAWINGS

FIG. 1A illustrates normal USH2A mRNA splicing of exons 40 and 41, resulting in wild-type USH2A protein.

FIG. 1B illustrates the deep intronic USH-causing mutation is an A-to-G transition (underlined and indicated with an asterisk) in intron 40 of USH2A.

FIG. 1C illustrates that upon binding of sequence-specific AONs, factors involved in splicing will not recognize the aberrant splice donor site in intron 40, resulting in redirection of normal USH2A splicing and synthesis of a correct USH2A protein.

FIG. 2A illustrates RT-PCR analysis of RHO ex3-USH2A PE40 wildtype/mutant-RHO ex5 mRNAs.

DETAILED DESCRIPTION

Figure 2B:
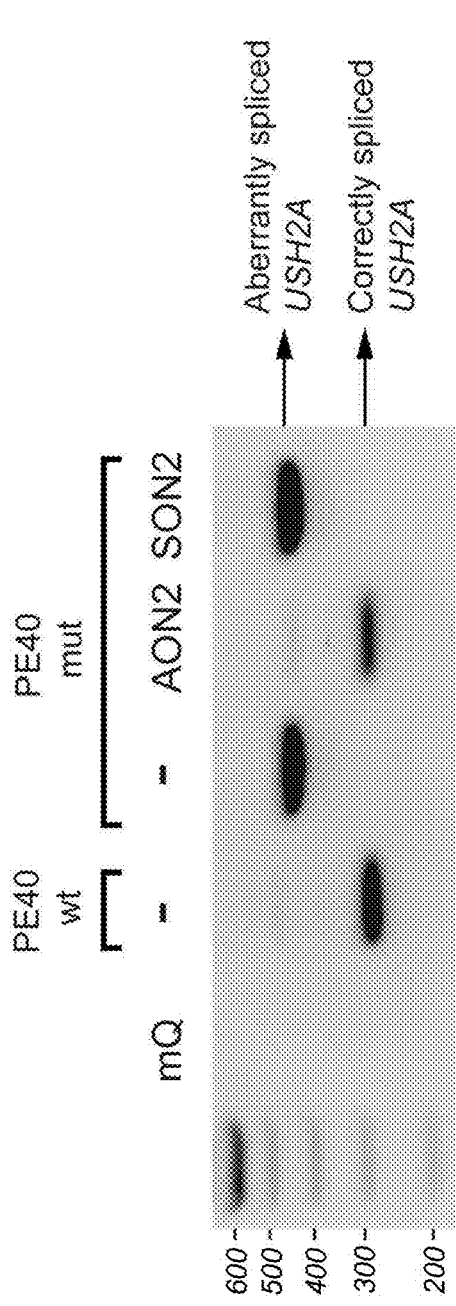
FIG. 2B) Specificity of AON-based rescue.

Surprisingly, it has now been demonstrated that specific antisense oligonucleotides (AONs) are able to block the aberrant splicing of USH2A that is caused by the intronic c.7595-2144A>G mutation leading to the inclusion of pseudoexon 40 (PE40), the inclusion of aberrant exon 13 or the inclusion of aberrant exon 50.

Accordingly, in a first aspect the invention provides an exon skipping molecule or an exon 12 retention molecule that binds to and/or is complementary to a polynucleotide with the nucleotide sequence as shown SEQ ID NO: 8, preferably selected from the group consisting of SEQ ID NO: 12, SEQ ID NO: 13 and SEQ ID NO: 14, more preferably selected from the group consisting of SEQ ID NO: 19, SEQ ID NO: 20, SEQ ID NO: 21, SEQ ID NO: 22, SEQ ID NO: 23 and SEQ ID NO: 24, most preferably selected from the group consisting of SEQ ID NO: 26, SEQ ID NO: 27, SEQ ID NO: 28, SEQ ID NO: 29, SEQ ID NO: 30, SEQ ID NO: 31, SEQ ID NO: 40 and SEQ ID NO: 41 or a part thereof.

In all embodiments of the invention, the terms "modulating splicing" and "exon skipping" are synonymous. In respect of USH2A, "modulating splicing" or "exon skipping" are to be construed as the exclusion of the aberrant 152 nucleotide pseudoexon (SEQ ID NO: 5), the exclusion of aberrant exon 13 or the exclusion of aberrant exon 50 in the USH2A mRNA, or restoring of the reading frame of the mRNA which includes the pseudoexon. In addition, there is provided for the retention of exon 12, preferably when exon 13 is skipped.

For the purpose of the invention the terms "the inclusion of aberrant pseudoexon", "the inclusion of aberrant pseudoexon 40" or "the inclusion of aberrant 152 bp nucleotide pseudoexon" are considered to be synonymous, and considered to mean the inclusion of pseudoexon 40 of the USH2A gene (SEQ ID NO: 5) into the mRNA, or the inclusion of a part thereof or a sequence comprising 90, 91, 92, 93, 94, 95, 96, 97, 98, 99 or 100% of SEQ ID NO:5 into the USH2A mRNA.

For the purpose of the invention the terms "aberrant exon 13" or "aberrant USH2A exon 13" are considered to be synonymous, and considered to mean the presence of a mutation in exon 13 (SEQ ID NO: 32) of the USH2A gene, resulting in an USH2A mRNA with at least one substitution, deletion or insertion in exon 13 of USH2A (SEQ ID NO: 32)

For the purpose of the invention the term "aberrant exon 50" or "aberrant USH2A exon 50" are considered to be synonymous, and considered to mean the presence of a mutation in exon 50 (SEQ ID NO: 33) of the USH2A gene, resulting in in an USH2A mRNA with at least one substitution, deletion or insertion in exon 50 of USH2A (SEQ ID NO: 33)

The term exon skipping is herein defined as inducing, producing or increasing production within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as exon skipping molecules. The term pre-mRNA refers to a non-processed or partly processed precursor mRNA that is synthesized from a DNA template of a cell by transcription, such as in the nucleus.

The term exon retention is herein defined as inducing, producing or increasing production within a cell of a mature mRNA that does retain a particular exon that should be present in the mature mRNA without exon skipping. Exon retention is achieved by providing a cell expressing the pre-mRNA of said mature mRNA with a molecule capable of interfering with sequences such as, for example, the intronic splice silencer sites in intron 12; such molecule is herein referred to as an exon retention molecule.

The term "antisense oligonucleotide" is understood to refer to a nucleotide sequence which is substantially complementary to a target nucleotide sequence in a pre-mRNA molecule, hnRNA (heterogenous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

The terms "antisense oligonucleotide" and "oligonucleotide" are used interchangeably herein and are understood to refer to an oligonucleotide comprising an antisense sequence.

In an embodiment, an exon skipping molecule or an exon 12 retention molecule as defined herein can be a compound molecule that binds and/or is complementary to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zincfinger proteins that bind specific nucleotide sequences are disclosed by Friesen and Darby, Nature Structural Biology 5: 543-546 (1998) which is herein incorporated by reference. Binding to one of the specified SEQ ID NO: 8, 12, 13, 14, 19, 20, 21, 22, 23, 24, 26, 27, 28, 29, 30, 31, 40 and 41 sequences, preferably in the context of the aberrant 152 nucleotide USH2A pseudoexon (SEQ ID NO: 5), the aberrant USH2A exon 13, the aberrant USH2A exon 50 or exon 12 may be assessed via techniques known to the skilled person. A preferred technique is gel mobility shift assay as described in EP 1 619 249. In a preferred embodiment, an exon skipping molecule or exon 12 retention molecule is said to bind to one of the specified sequences as soon as a binding of said molecule to a labeled sequence SEQ ID NO: 8, 12, 13, 14, 19, 20, 21, 22, 23, 24, 26, 27, 28, 29, 30, 31, 40 and 41 is detectable in a gel mobility shift assay.

In all embodiments of the invention, an exon skipping molecule or exon retention molecule is preferably a nucleic acid molecule, preferably an oligonucleotide. Preferably, an exon skipping molecule according to the invention is a nucleic acid molecule, preferably an oligonucleotide, which is complementary or substantially complementary to a nucleotide sequence as shown in SEQ ID NO: 8, or preferably selected from the group consisting of SEQ ID NO: 12, SEQ ID NO: 13 and SEQ ID NO: 14, or more preferably selected from the group consisting of SEQ ID NO: 19, SEQ ID NO: 20, SEQ ID NO: 21, SEQ ID NO: 22, SEQ ID NO: 23 and SEQ ID NO: 24 sequences, or most preferably selected from the group consisting of SEQ ID NO: 26, SEQ ID NO: 27, SEQ ID NO: 28, SEQ ID NO: 29, SEQ ID NO: 30 and SEQ ID NO: 31, or a part thereof as later defined herein. Preferably, an exon 12 retention molecule according to the invention is a nucleic acid molecule, preferably an oligonucleotide, which is complementary or substantially complementary to a nucleotide sequence as shown in SEQ ID NO: 40 or more preferably SEQ ID NO: 41, or a part thereof as later defined herein.

The term "substantially complementary" used in the context of the invention indicates that some mismatches in the antisense sequence are allowed as long as the functionality, i.e. inducing skipping of the 152 nucleotide USH2A pseudoexon (SEQ ID NO: 5), the aberrant USH2A exon 13 or the aberrant USH2A exon 50, or retention of exon 12 is still acceptable. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

The invention provides a method for designing an exon skipping molecule or an exon retention molecule, preferably an oligonucleotide able to induce skipping of the aberrant 152 nucleotide USH2A pseudoexon (SEQ ID NO: 5), the aberrant USH2A exon 13 or the aberrant USH2A exon 50, or able to induce retention of exon 12. First, said oligonucleotide is selected to bind to one of SEQ ID NO: 8, 12, 13, 14, 19, 20, 21, 22, 23, 24, 26, 27, 28, 29, 30, 31, 40 and 41 or a part thereof as defined later herein. Subsequently, in a preferred method at least one of the following aspects has to be taken into account for designing, improving said exon skipping molecule any further:

The exon skipping molecule preferably does not contain a CpG or a stretch of CpG, The exon skipping molecule has acceptable RNA binding kinetics and/or thermodynamic properties.

The presence of a CpG or a stretch of CpG in an oligonucleotide is usually associated with an increased immunogenicity of said oligonucleotide (Dorn and Kippenberger, 2008). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person. An inflammatory reaction, type I-like interferon production, IL-12 production and/or an increase in immunogenicity may be assessed by detecting the presence or an increasing amount of a neutralizing antibody or an antibody recognizing said oligonucleotide using a standard immunoassay.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/-cail/biotool/oligo/index.html) for single stranded RNA using the basic Tm and the nearest neighbor model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 70° C. and an acceptable free energy may be ranged between 15 and 45 kcal/mol.

The skilled person may therefore first choose an oligonucleotide as a potential therapeutic compound as binding and/or being complementary to SEQ ID NO: 8, 12, 13, 14, 19, 20, 21, 22, 23, 24, 26, 27, 28, 29, 30, 31, 40, or 41 or a part thereof as defined later herein. The skilled person may check that said oligonucleotide is able to bind to said sequences as earlier defined herein. Optionally in a second step, he may use the invention to further optimize said oligonucleotide by checking for the absence of CpG and/or by optimizing its Tm and/or free energy of the AON-target complex. He may try to design an oligonucleotide wherein few, preferably, no CpG and/or wherein a more acceptable Tm and/or free energy are obtained by choosing a distinct sequence of USH2A (including SEQ ID NO: 8, 12, 13, 14, 19, 20, 21, 22, 23, 24, 26, 27, 28, 29, 30, 31, 40 or 41) to which the oligonucleotide is complementary. Alternatively, if an oligonucleotide complementary to a given stretch within SEQ ID NO: 8, 12, 13, 14, 19, 20, 21, 22, 23, 24, 26, 27, 28, 29, 30, 31, 40 or 41, comprises a CpG, and/or does not have an acceptable Tm and/or free energy, the skilled person may improve any of these parameters by decreasing the length of the oligonucleotide, and/or by choosing a distinct stretch within any of SEQ ID NO: 8, 12, 13, 14, 19, 20, 21, 22, 23, 24, 26, 27, 28, 29, 30, 31, 40 or 41 to which the oligonucleotide is complementary and/or by altering the chemistry of the oligonucleotide.

At any step of the method, an oligonucleotide of the invention is preferably an olignucleotide, which is still able to exhibit an acceptable level of functional activity. A functional activity of said oligonucleotide is preferably to induce the skipping of the aberrant 152 nucleotide USH2A pseudoexon (SEQ ID NO: 5), the aberrant USH2A exon 13 or the aberrant USH2A exon 50 to a certain extent and/or the retention of exon 12, to provide an individual with a functional USH2A protein and/or mRNA and/or at least in part decreasing the production of an aberrant USH2A protein and/or mRNA.

In a preferred embodiment, an oligonucleotide is said to induce skipping of the aberrant 152 nucleotide USH2A pseudoexon (SEQ ID NO: 5), when the aberrant 152 nucleotide USH2A pseudoexon (SEQ ID NO: 5) skipping percentage as measured by real-time quantitative RT-PCR analysis is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

In another preferred embodiment, an oligonucleotide is said to induce skipping of the aberrant USH2A exon 13, when the aberrant USH2A exon 13 skipping percentage as measured by real-time quantitative RT-PCR analysis is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

In another preferred embodiment, an oligonucleotide is said to induce skipping of the aberrant USH2A exon 50, when the aberrant USH2A exon 50 skipping percentage as measured by real-time quantitative RT-PCR analysis is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

In an embodiment, an oligonucleotide is said to induce retention of exon 12, when the exon 12 retention percentage as measured by real-time quantitative RT-PCR analysis is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

Preferred assays to determine exon skipping and/or exon retention are described in the examples herein.

Preferably, a nucleic acid molecule according to the invention, preferably an oligonucleotide, which comprises a sequence that is complementary or substantially complementary to a nucleotide sequence as shown in SEQ ID NO: 8, or preferably selected from the group consisting of SEQ ID NO: 12, SEQ ID NO: 13 and SEQ ID NO: 14, or more preferably selected from the group consisting of SEQ ID NO: 19, SEQ ID NO: 20, SEQ ID NO: 21, SEQ ID NO: 22, SEQ ID NO: 23 and SEQ ID NO: 24, or most preferably selected from the group consisting of SEQ ID NO: 26, SEQ ID NO: 27, SEQ ID NO: 28, SEQ ID NO: 29, SEQ ID NO: 30, SEQ ID NO: 31, SEQ ID NO: 40 and SEQ ID NO: 41, or part thereof of USH2A is such that the (substantially) complementary part is at least 50% of the length of the oligonucleotide according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. Preferably, an oligonucleotide according to the invention comprises or consists of a sequence that is complementary to part of SEQ ID NO: 8, 12, 13, 14, 19, 20, 21, 22, 23, 24, 26, 27, 28, 29, 30, 31, 40 or 41. As an example, an oligonucleotide may comprise a sequence that is complementary to part of SEQ ID NO: 8, 12, 13, 14, 19, 20, 21, 22, 23, 24, 26, 27, 28, 29, 30, 31, 40 or 41 and additional flanking sequences.

In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides. Additional flanking sequences may be used to modify the binding of a protein to the oligonucleotide, or to modify a thermodynamic property of the oligonucleotide, more preferably to modify target RNA binding affinity.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" preferably means that using a gel mobility shift assay as described in example 1 of EP1619249, binding of an oligonucleotide is detectable.

Optionally, said oligonucleotide may further be tested by transfection into retina cells of patients. Skipping of a targeted exon or retention of exon 12 may be assessed by RT-PCR (such as e.g. described in EP1619249). The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide. It is clear that oligonucleotides comprising mismatches in the region of complementarity but that retain the capacity to hybridize and/or bind to the targeted region(s) in the pre-mRNA, can be used in the invention. However, preferably at least the complementary parts do not comprise such mismatches as oligonucleotides lacking mismatches in the complementary part typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

An exon skipping molecule of the invention is preferably an isolated molecule. An exon skipping molecule of the invention is preferably a nucleic acid molecule or nucleotide-based molecule, preferably an (antisense) oligonucleotide, which is complementary to a sequence selected from SEQ ID NO: 8, 12, 13, 14, 19, 20, 21, 22, 23, 24, 26, 27, 28, 29, 30, 31, 40 and 41.

A preferred exon skipping molecule or exon 12 retention molecule according to the invention is a nucleic acid molecule comprising an antisense oligonucleotide which antisense oligonucleotide has a length from about 8 to about 143 nucleotides, more preferred from about 8 to 60, more preferred 10 to about 40 nucleotides, more preferred from about 12 to about 30 nucleotides, more preferred from about 14 to about 28 nucleotides, nucleotides, most preferred about 20 nucleotides, such as 15 nucleotides, 16 nucleotides, 17 nucleotides, 18 nucleotides, 19 nucleotides, 20 nucleotides, 21 nucleotides, 22 nucleotides, 23 nucleotides, 24 nucleotides or 25 nucleotides.

A preferred exon skipping molecule or exon 12 retention molecule of the invention is an antisense oligonucleotide comprising or consisting of from 8 to 143 nucleotides, more preferred from 10 to 40 nucleotides, more preferred from 12 to 30 nucleotides, more preferred from 14 to 20 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In certain embodiments, the invention provides an exon skipping molecule comprising or preferably consisting of an antisense oligonucleotide selected from the group consisting of SEQ ID NO: 10, SEQ ID NO: 11, SEQ ID NO: 15, SEQ ID NO: 16, SEQ ID NO: 17 and SEQ ID NO: 18. In certain embodiments, the invention provides an exon 12 retention molecule comprising or preferably consisting of antisense oligonucleotide SEQ ID NO: 39.

In a more preferred embodiment, the invention provides an exon skipping molecule comprising or preferably consisting of the antisense oligonucleotide SEQ ID NO: 10. It was found that this molecule is very efficient in modulating splicing of the aberrant 152 nucleotide USH2A pseudoexon. This preferred exon skipping molecule of the invention comprising SEQ ID NO: 10 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 11. It was found that this molecule is very efficient in modulating splicing of the aberrant 152 nucleotide USH2A pseudoexon. This preferred exon skipping molecule of the invention comprising SEQ ID NO: 11 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In a more preferred embodiment, the invention provides an exon skipping molecule comprising or preferably consisting of the antisense oligonucleotide SEQ ID NO: 15. It was found that this molecule is very efficient in modulating splicing of the aberrant USH2A exon 13. This preferred exon skipping molecule of the invention comprising SEQ ID NO: 15 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In a more preferred embodiment, the invention provides an exon skipping molecule comprising or preferably consisting of the antisense oligonucleotide SEQ ID NO: 16. It was found that this molecule is very efficient in modulating splicing of the aberrant USH2A exon 13. This preferred exon skipping molecule of the invention comprising SEQ ID NO: 16 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In a more preferred embodiment, the invention provides an exon skipping molecule comprising or preferably consisting of the antisense oligonucleotide SEQ ID NO: 17. It was found that this molecule is very efficient in modulating splicing of the aberrant USH2A exon 50. This preferred exon skipping molecule of the invention comprising SEQ ID NO: 17 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In a more preferred embodiment, the invention provides an exon skipping molecule comprising or preferably consisting of the antisense oligonucleotide SEQ ID NO: 18. It was found that this molecule is very efficient in modulating splicing of the aberrant USH2A exon 50. This preferred exon skipping molecule of the invention comprising SEQ ID NO: 18 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

An exon skipping molecule or an exon 12 retention molecule according to the invention may contain one of more RNA residues, or one or more DNA residues, and/or one or more nucleotide analogues or equivalents, as will be further detailed herein below.

It is preferred that an exon skipping molecule or exon 12 retention molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents.

Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568). A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred exon skipping molecule according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives. An effective antisense oligonucleotide according to the invention comprises a 2'-O-methyl ribose with a phosphorothioate backbone.

It will also be understood by a skilled person that different antisense oligonucleotides can be combined for efficiently skipping of the aberrant 152 nucleotide pseudoexon of USH2A, the aberrant USH2A exon 13 or the aberrant USH2A exon 50. In a preferred embodiment, a combination of at least two antisense oligonucleotides are used in a method of the invention, such as two different antisense oligonucleotides, three different antisense oligonucleotides, four different antisense oligonucleotides, or five different antisense oligonucleotides. A preferred set of exon skipping molecules comprises an antisense oligonucleotide according to the invention, which comprises a sequence that is complementary or substantially complementary to a nucleotide sequence as shown in SEQ ID NO: 19 and an antisense oligonucleotide according to the invention, which comprises a sequence that is complementary or substantially complementary to a nucleotide sequence as shown in SEQ ID NO: 20. A further preferred set of exon skipping molecules comprises an antisense oligonucleotide according to the invention, which comprises a sequence that is complementary or substantially complementary to a nucleotide sequence as shown in SEQ ID NO: 21 and an antisense oligonucleotide according to the invention, which comprises a sequence that is complementary or substantially complementary to a nucleotide sequence as shown in SEQ ID NO: 22. A further preferred set of exon skipping molecules comprises an antisense oligonucleotide according to the invention, which comprises a sequence that is complementary or substantially complementary to a nucleotide sequence as shown in SEQ ID NO: 23 and an antisense oligonucleotide according to the invention, which comprises a sequence that is complementary or substantially complementary to a nucleotide sequence as shown in SEQ ID NO: 24. A more preferred set of exon skipping molecules comprises an antisense oligonucleotide according to the invention, which comprises a sequence that is complementary or substantially complementary to a nucleotide sequence as shown in SEQ ID NO: 26 and an antisense oligonucleotide according to the invention, which comprises a sequence that is complementary or substantially complementary to a nucleotide sequence as shown in SEQ ID NO: 27. A further more preferred set of exon skipping molecules comprises an antisense oligonucleotide according to the invention, which comprises a sequence that is complementary or substantially complementary to a nucleotide sequence as shown in SEQ ID NO: 28 and an antisense oligonucleotide according to the invention, which comprises a sequence that is complementary or substantially complementary to a nucleotide sequence as shown in SEQ ID NO: 29. A further more preferred set of exon skipping molecules comprises an antisense oligonucleotide according to the invention, which comprises a sequence that is complementary or substantially complementary to a nucleotide sequence as shown in SEQ ID NO: 30 and an antisense oligonucleotide according to the invention, which comprises a sequence that is complementary or substantially complementary to a nucleotide sequence as shown in SEQ ID NO: 31. An even more preferred set of exon skipping molecules comprises an exon skipping molecule according to the invention comprising or preferably consisting of the antisense oligonucleotide SEQ ID NO: 10 and an exon skipping molecule according to the invention comprising or preferably consisting of the antisense oligonucleotide SEQ ID NO: 11. A further even more preferred set of exon skipping molecules comprises an exon skipping molecule according to the invention comprising or preferably consisting of the antisense oligonucleotide SEQ ID NO: 15 and an exon skipping molecule according to the invention comprising or preferably consisting of the antisense oligonucleotide SEQ ID NO: 16. A further even more preferred set of exon skipping molecules comprises an exon skipping molecule according to the invention comprising or preferably consisting of the antisense oligonucleotide SEQ ID NO: 17 and an exon skipping molecule according to the invention comprising or preferably consisting of the antisense oligonucleotide SEQ ID NO: 18.

Skipping of exon 13 may lead to the inadvertent skipping of exon 12 as well. Accordingly, there is provided a retention molecule for exon 12. A preferred exon 12 retention molecule according to the invention is a nucleic acid molecule, preferably an oligonucleotide which is complementary or substantially complementary to a nucleotide sequence as shown in SEQ ID NO: 40, more preferably to a nucleotide sequence as shown in SEQ ID NO: 41. A more preferred exon 12 retention molecule according to the invention is an oligonucleotide comprising or preferably consisting of the antisense oligonucleotide SEQ ID NO: 39.

In an embodiment, the invention provides an exon 12 retention molecule comprising or preferably consisting of the antisense oligonucleotide SEQ ID NO: 39. It was found that this molecule is very efficient in retention of exon 12. This preferred exon 12 retention molecule according to the invention comprising SEQ ID NO: 39 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

Said exon 12 retention molecule according to the invention is preferably combined with an exon skipping molecule according to the invention for skipping of exon 13. A preferred combination of an exon 12 retention molecule according to the invention and an exon 13 skipping molecule according to the invention comprises an antisense oligonucleotide according to the invention, which comprises a sequence that is complementary or substantially complementary to a nucleotide sequence as shown in SEQ ID NO: 40 and an antisense oligonucleotide according to the invention which comprises a sequence that is complementary or substantially complementary to a nucleotide sequence as shown in SEQ ID NO: 21. A further preferred combination of an exon 12 retention molecule according to the invention and an exon 13 skipping molecule according to the invention comprises an antisense oligonucleotide according to the invention which comprises a sequence that is complementary or substantially complementary to a nucleotide sequence as shown in SEQ ID NO: 40 and an antisense oligonucleotide according to the invention which comprises a sequence that is complementary or substantially complementary to a nucleotide sequence as shown in SEQ ID NO: 22. A more preferred combination of an exon 12 retention molecule according to the invention and an exon 13 skipping molecule according to the invention comprises an antisense oligonucleotide according to the invention which comprises a sequence that is complementary or substantially complementary to a nucleotide sequence as shown in SEQ ID NO: 40, an antisense oligonucleotide according to the invention which comprises a sequence that is complementary or substantially complementary to a nucleotide sequence as shown in SEQ ID NO: 21 and an antisense oligonucleotide according to the invention which comprises a sequence that is complementary or substantially complementary to a nucleotide sequence as shown in SEQ ID NO: 22. A further more preferred combination of an exon 12 retention molecule according to the invention and an exon 13 skipping molecule according to the invention comprises an antisense oligonucleotide according to the invention, which comprises a sequence that is complementary or substantially complementary to a nucleotide sequence as shown in SEQ ID NO: 41 and an antisense oligonucleotide according to the invention which comprises a sequence that is complementary or substantially complementary to a nucleotide sequence as shown in SEQ ID NO: 28. A further more preferred combination of an exon 12 retention molecule according to the invention and an exon 13 skipping molecule according to the invention comprises an antisense oligonucleotide according to the invention, which comprises a sequence that is complementary or substantially complementary to a nucleotide sequence as shown in SEQ ID NO: 41 and an antisense oligonucleotide according to the invention which comprises a sequence that is complementary or substantially complementary to a nucleotide sequence as shown in SEQ ID NO: 29. A even more preferred combination of an exon 12 retention molecule according to the invention and an exon 13 skipping molecule according to the invention comprises an antisense oligonucleotide according to the invention, which comprises a sequence that is complementary or substantially complementary to a nucleotide sequence as shown in SEQ ID NO: 41, an antisense oligonucleotide according to the invention which comprises a sequence that is complementary or substantially complementary to a nucleotide sequence as shown in SEQ ID NO: 28 and an antisense oligonucleotide according to the invention which comprises a sequence that is complementary or substantially complementary to a nucleotide sequence as shown in SEQ ID NO: 29.

An even more preferred combination of an exon 12 retention molecule according to the invention and an exon 13 skipping molecule according to the invention comprises an oligonucleotide comprising or preferably consisting of the antisense oligonucleotide SEQ ID NO: 39 and an exon skipping molecule according to the invention comprising or preferably consisting of the antisense oligonucleotide SEQ ID NO: 15. A further even more preferred combination of an exon 12 retention molecule according to the invention and an exon 13 skipping molecule according to the invention comprises an oligonucleotide comprising or preferably consisting of the antisense oligonucleotide SEQ ID NO: 39 and an exon skipping molecule according to the invention comprising or preferably consisting of the antisense oligonucleotide SEQ ID NO: 16. A further even more preferred combination of an exon 12 retention molecule according to the invention and an exon 13 skipping molecule according to the invention comprises an oligonucleotide comprising or preferably consisting of the antisense oligonucleotide SEQ ID NO: 39, an exon skipping molecule according to the invention comprising or preferably consisting of the antisense oligonucleotide SEQ ID NO: 15 and an exon skipping molecule according to the invention comprising or preferably consisting of the antisense oligonucleotide SEQ ID NO: 16. In all embodiments of the invention relating to skipping of exon 13 it is to be understood that skipping of exon 13 can be combined with the retention of exon 12 with an exon 12 retention molecule provided herein.

An antisense oligonucleotide can be linked to a moiety that enhances uptake of the antisense oligonucleotide in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An exon skipping molecule or exon 12 retention molecule according to the invention may be indirectly administered using suitable means known in the art. When the exon skipping molecule or exon 12 retention molecule is an oligonucleotide, it may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an exon skipping molecule or exon 12 retention molecule as identified herein. Accordingly, the invention provides a viral vector expressing an exon skipping molecule or exon 12 retention molecule according to the invention when placed under conditions conducive to expression of the exon skipping molecule. A cell can be provided with an exon skipping molecule capable of interfering with essential sequences that result in highly efficient skipping of the aberrant 152 nucleotide USH2A pseudoexon, the aberrant USH2A exon 13 or the aberrant USH2A exon 50 by plasmid-derived antisense oligonucleotide expression or viral expression provided by adenovirus- or adeno-associated virus-based vectors. Likewise exon 12 retention can be mediated by plasmid-derived antisense oligonucleotide expression or viral expression provided by adenovirus- or adeno-associated virus-based vectors. Expression may be driven by a polymerase II-promoter (Pol II) such as a U7 promoter or a polymerase III (Pol III) promoter, such as a U6 RNA promoter. A preferred delivery vehicle is a viral vector such as an adenoassociated virus vector (AAV), or a retroviral vector such as a lentivirus vector and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts, preferably, in the form of a fusion transcript with an U1 or U7 transcript. Such fusions may be generated as described (Gorman L et al, 1998 or Suter D et al, 1999).

The exon skipping molecule or exon 12 retention molecule according to the invention, preferably an antisense oligonucleotide, may be delivered as such. However, the exon skipping molecule or exon 12 retention molecule may also be encoded by the viral vector. Typically, this is in the form of an RNA transcript that comprises the sequence of an oligonucleotide according to the invention in a part of the transcript.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of the aberrant 152 nucleotide USH2A pseudoexon, the aberrant USH2A exon 13 or the aberrant USH2A exon 50 or for effective retention of exon 12.

A preferred AAV-based vector for instance comprises an expression cassette that is driven by a polymerase III-promoter (Pol III) or a polymerase II-promoter (Pol II). A preferred RNA promoter is, for example, a Pol III U6 RNA promoter, or a Pol II U7 RNA promoter.

The invention therefore also provides a viral-based vector, comprising a Pol II or a Pol III promoter driven expression cassette for expression of an antisense oligonucleotide of the invention for inducing skipping of aberrant 152 nucleotide USH2A pseudoexon, the aberrant USH2A exon 13 or the aberrant USH2A exon 50 or for retention of exon 12.

An AAV vector according to the invention is a recombinant AAV vector and refers to an AAV vector comprising part of an AAV genome comprising an encoded exon skipping molecule or exon 12 retention molecule according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. Protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention.

Preferably, a recombinant AAV vector according to the invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector.

More preferably, a recombinant AAV vector according to the invention comprises a capsid protein shell of AAV serotype 2 and the AAV genome or ITRs present in said vector are derived from AAV serotype 5; such vector is referred to as an AAV 2/5 vector.

More preferably, a recombinant AAV vector according to the invention comprises a capsid protein shell of AAV serotype 2 and the AAV genome or ITRs present in said vector are derived from AAV serotype 8; such vector is referred to as an AAV 2/8 vector.

More preferably, a recombinant AAV vector according to the invention comprises a capsid protein shell of AAV serotype 2 and the AAV genome or ITRs present in said vector are derived from AAV serotype 9; such vector is referred to as an AAV 2/9 vector.

More preferably, a recombinant AAV vector according to the invention comprises a capsid protein shell of AAV serotype 2 and the AAV genome or ITRs present in said vector are derived from AAV serotype 2; such vector is referred to as an AAV 2/2 vector.

A nucleic acid molecule encoding an exon skipping molecule or exon 12 retention molecule according to the invention represented by a nucleic acid sequence of choice is preferably inserted between the AAV genome or ITR sequences as identified above, for example an expression construct comprising an expression regulatory element operably linked to a coding sequence and a 3' termination sequence.

"AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on a AAV helper construct, which may be a plasmid. Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

Preferably, an AAV genome as present in a recombinant AAV vector according to the invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

Preferably, an AAV vector according to the invention is constructed and produced according to the methods in the Examples herein.

A preferred AAV vector according to the invention is an AAV vector, preferably an AAV2/5, AAV2/8, AAV2/9 or AAV2/2 vector, expressing an exon skipping molecule or an exon 12 retention molecule according to the invention that is an antisense oligonucleotide that comprises, or preferably consists of, a sequence that is complementary or substantially complementary to a nucleotide sequence as shown in SEQ ID NO: 8, or preferably selected from the group consisting of SEQ ID NO: 12, SEQ ID NO: 13 and SEQ ID NO: 14, or more preferably selected from the group consisting of SEQ ID NO: 19, SEQ ID NO: 20, SEQ ID NO: 21, SEQ ID NO: 22, SEQ ID NO: 23 and SEQ ID NO: 24, or most preferably selected from the group consisting of SEQ ID NO: 26, SEQ ID NO: 27, SEQ ID NO: 28, SEQ ID NO: 29, SEQ ID NO: 30, SEQ ID NO: 31, SEQ ID NO: 40 and SEQ ID NO: 41.

A further preferred AAV vector according to the invention is an AAV vector, preferably an AAV2/5, AAV2/8, AAV2/9 or AAV2/2 vector, expressing an exon skipping molecule or an exon 12 retention molecule according to the invention that is an antisense oligonucleotide that comprises, or preferably consists of, SEQ ID NO: 10, 11, 15, 16, 17, 18 or 39.

Figure 7:
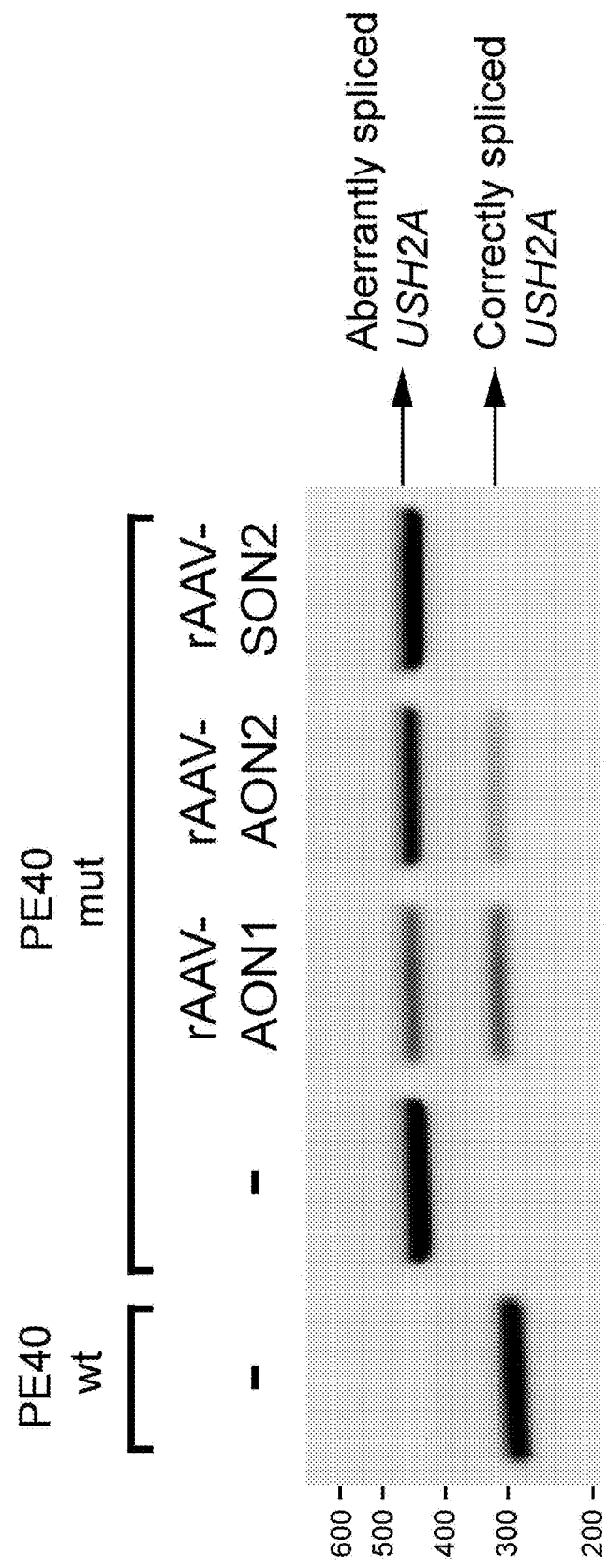
FIG. 7 illustrates RT-PCR analysis of RHO ex3-USH2A PE40 wildtype/mutant-RHO ex5 mRNA's isolated from transfected HEK293T cells that were cultured in the absence or presence of 1.0 µg pSMD2-U7-USH2A PE40-AON1 (SEQ ID NO: 42) or pSMD2-U7-USH2A PE40-AON2 (SEQ ID NO: 43) directed against the aberrant USH2A PE40 exon. As a negative control, 1.0 µg of the pSMD2-U7-USH2A PE40-SON2 (SEQ ID NO: 44) was transfected.

A further preferred AAV vector according to the invention, preferably an AAV2/5, AAV2/8, AAV2/9 or AAV2/2 vector, is a virion corresponding to one of rAAV-AON1 and rAAV-AON2, as depicted in FIG. 7 as constructed and produced in the examples.

Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to an individual, a cell, tissue or organ of said individual. When administering an exon skipping molecule according to the invention, it is preferred that the molecule is dissolved in a solution that is compatible with the delivery method. Retina or inner ear cells can be provided with a plasmid for antisense oligonucleotide expression by providing the plasmid in an aqueous solution.

Alternatively, a preferred delivery method for an antisense oligonucleotide or a plasmid for antisense oligonucleotide expression is a viral vector or nanoparticles. Preferably viral vectors or nanoparticles are delivered to retina or inner ear cells. Such delivery to retina or inner ear cells or other relevant cells may be in vivo, in vitro or ex vivo.

Alternatively, a plasmid can be provided by transfection using known transfection agentia. For intravenous, subcutaneous, intramuscular, intrathecal and/or intraventricular administration it is preferred that the solution is a physiological salt solution. Particularly preferred in the invention is the use of an excipient or transfection agentia that will aid in delivery of each of the constituents as defined herein to a cell and/or into a cell, preferably a retina cell. Preferred are excipients or transfection agentia capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constitutent as defined herein to a cell, preferably a retina cell. Such excipients have been shown to efficiently deliver an oligonucleotide such as antisense nucleic acids to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N, N, N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such as diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a USH2A related disease or condition. "Prevention, treatment or delay of a USH2A related disease or condition" is herein preferably defined as preventing, halting, ceasing the progression of, or reversing partial or complete visual impairment or blindness, as well as preventing, halting, ceasing the progression of or reversing partial or complete auditory impairment or deafness that is caused by a genetic defect in the USH2A gene.

In addition, an exon skipping molecule or exon 12 retention molecule according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule or exon 12 retention molecule according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an exon skipping molecule according to the invention and a further adjunct compound as later defined herein.

If required, an exon skipping molecule or exon 12 retention molecule according to the invention or a vector, preferably a viral vector, expressing an exon skipping molecule or exon 12 retention molecule according to the invention can be incorporated into a pharmaceutically active mixture by adding a pharmaceutically acceptable carrier.

Accordingly, the invention also provides a composition, preferably a pharmaceutical composition, comprising an exon skipping molecule or exon 12 retention molecule according to the invention, or a viral vector according to the invention and a pharmaceutically acceptable excipient. Such composition may comprise a single exon skipping molecule, exon 12 retention molecule or viral vector according to the invention, but may also comprise multiple, distinct exon skipping molecules, exon 12 retention molecules or viral vectors according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

A preferred route of administration is through intra-vitreal injection of an aqueous solution or specially adapted formulation for intraocular administration. EP 2 425 814 discloses an oil in water emulsion especially adapted for intraocular (intravitreal) administration of peptide or nucleic acid drugs. This emulsion is less dense than the vitreous fluid, so that the emulsion floats on top of the vitreous, avoiding that the injected drug impairs vision.

If multiple distinct exon skipping molecules according to the invention are used, optionally combined with an exon 12 retention molecule according to the invention, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules and or exon 12 skipping molecules according to the invention used is dosed in an amount ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg.

A preferred exon skipping molecule and/or exon retention molecule according to the invention, is for the treatment of a USH2A related disease or condition of an individual. In all embodiments of the invention, the term "treatment" is understood to include the prevention and/or delay of the USH2A related disease or condition. An individual, which may be treated using an exon skipping molecule and/or exon 12 retention molecule according to the invention may already have been diagnosed as having a USH2A related disease or condition.

Alternatively, an individual which may be treated using an exon skipping molecule and/or exon 12 retention molecule according to the invention may not have yet been diagnosed as having a USH2A related disease or condition but may be an individual having an increased risk of developing a USH2A related disease or condition in the future given his or her genetic background. A preferred individual is a human being. In a preferred embodiment the USH2A related disease or condition is Usher Syndrome type 2.

Accordingly, the invention further provides an exon skipping molecule and/or an exon 12 retention molecule according to the invention, or a viral vector according to the invention, or a composition according to the invention for use as a medicament, for treating a USH2A related disease or condition requiring modulating splicing of USH2A and for use as a medicament for the prevention, treatment or delay of a USH2A related disease or condition. A preferred USH2A related disease or condition is Usher Syndrome type 2. Each feature of said use has earlier been defined herein.

The invention further provides the use of an exon skipping molecule and/or exon 12 retention molecule according to the invention, or of a viral vector according to the invention, or a composition according to the invention for the treatment of a USH2A related disease or condition requiring modulating splicing of USH2A. In a preferred embodiment the USH2A related disease or condition is Usher Syndrome type 2.

The invention further provides the use of an exon skipping molecule and/or exon 12 retention molecule according to the invention, or of a viral vector according to the invention, or a composition according to the invention for the preparation of a medicament, for the preparation of a medicament for treating a USH2A related disease or condition requiring modulating splicing of USH2A and for the preparation of a medicament for the prevention, treatment or delay of a USH2A related disease or condition. A preferred USH2A related disease or condition is Usher Syndrome type 2. Therefore in a further aspect, there is provided the use of an exon skipping molecule and/or exon 12 retention molecule, viral vector or composition as defined herein for the preparation of a medicament, for the preparation of a medicament for treating a condition requiring modulating splicing of USH2A and for the preparation of a medicament for the prevention, treatment or delay of a USH2A related disease or condition. A preferred USH2A related disease or condition is Usher Syndrome type 2. Each feature of said use has earlier been defined herein.

A treatment in a use or in a method according to the invention is at least once, lasts one week, one month, several months, one year, 2, 3, 4, 5, 6 years or longer, such as lifelong. Each exon skipping molecule or exon skipping oligonucleotide or exon 12 retention molecule or equivalent thereof as defined herein for use according to the invention may be suitable for direct administration to a cell, tissue and/or an organ in vivo of individuals already affected or at risk of developing USH2A related disease or condition, and may be administered directly in vivo, ex vivo or in vitro. The frequency of administration of an oligonucleotide, composition, compound or adjunct compound of the invention may depend on several parameters such as the severity of the disease, the age of the patient, the mutation of the patient, the number of exon skipping molecules (i.e. dose), the formulation of said molecule, the route of administration and so forth. The frequency may vary between daily, weekly, at least once in two weeks, or three weeks or four weeks or five weeks or a longer time period.

Dose ranges of an exon skipping molecule or exon 12 retention molecule, preferably an oligonucleotide according to the invention are preferably designed on the basis of rising dose studies in clinical trials (in vivo use) for which rigorous protocol requirements exist. An exon skipping molecule or exon 12 retention molecule, preferably an oligonucleotide as defined herein, may be used at a dose which is ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg.

In a preferred embodiment, a concentration of an oligonucleotide as defined herein, which is ranged from 0.1 nM and 1 µM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nM. If several oligonucleotides are used, this concentration or dose may refer to the total concentration or dose of oligonucleotides or the concentration or dose of each oligonucleotide added.

In a preferred embodiment, a viral vector, preferably an AAV vector as described earlier herein, as delivery vehicle for a molecule according to the invention, is administered in a dose ranging from $1 \times 10^9$-$1 \times 10^{17}$ virus particles per injection, more preferably from $1 \times 10^{10}$-$1 \times 10^{12}$ virus particles per injection.

The ranges of concentration or dose of oligonucleotide(s) as given above are preferred concentrations or doses for in vivo, in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimized any further.

An exon skipping molecule or exon 12 retention molecule according to the invention, or a viral vector according to the invention, or a composition according to the invention for use according to the invention may be suitable for administration to a cell, tissue and/or an organ in vivo of individuals already affected or at risk of developing a USH2A related disease or condition, and may be administered in vivo, ex vivo or in vitro. Said exon skipping molecule or exon 12 retention molecule according to the invention, or a viral vector according to the invention, or a composition according to the invention may be directly or indirectly administered to a cell, tissue and/or an organ in vivo of an individual already affected by or at risk of developing a USH2A related disease or condition, and may be administered directly or indirectly in vivo, ex vivo or in vitro. As Usher Syndrome type 2 has a pronounced phenotype in retina and inner ear cells, it is preferred that said cells are retina or inner ear cells, it is further preferred that said tissue is the retina or the inner ear and/or it is further preferred that said organ comprises or consists of the eye or the ear.

The invention further provides a method for modulating splicing of USH2A in a cell comprising contacting the cell, preferably a retina cell, with an exon skipping molecule and/or an exon 12 retention molecule according to the invention, or a viral vector according to the invention, or a composition according to the invention. The features of this aspect are preferably those defined earlier herein. Contacting the cell with an exon skipping molecule according to the invention, or a viral vector according to the invention, or a composition according to the invention may be performed by any method known by the person skilled in the art. Use of the methods for delivery of exon skipping molecules, an exon 12 retention molecule, viral vectors and compositions described herein is included. Contacting may be directly or indirectly and may be in vivo, ex vivo or in vitro.

The invention further provides a method for the treatment of a USH2A related disease or condition requiring modulating splicing of USH2A of an individual in need thereof, said method comprising contacting a cell, preferably a retina cell, of said individual with an exon skipping molecule and/or an exon 12 retention molecule according to the invention, or a viral vector according to the invention, or a composition according to the invention. The features of this aspect are preferably those defined earlier herein. Contacting the cell, preferably a retina cell with an exon skipping molecule according to the invention, or a viral vector according to the invention, or a composition according to the invention may be performed by any method known by the person skilled in the art. Use of the methods for delivery of molecules, viral vectors and compositions described herein is included. Contacting may be directly or indirectly and may be in vivo, ex vivo or in vitro, A preferred USH2A related disease or condition is Usher Syndrome type 2.

Unless otherwise indicated each embodiment as described herein may be combined with another embodiment as described herein.

As can be observed in the experimental section herein, at the RNA level, addition of various AONs targeting the aberrant USH2A pseudoexon indeed resulted in exclusion of the USH2A pseudoexon from the pseudoexon containing rhodopsin construct. AONs are postulated to restore aberrant splicing in patient cells or cell lines as well, coinciding with an increased synthesis of the wild-type USH2A protein.

In nasal cells, USH2A is abundantly expressed. Therefore, it is postulated that addition of AONs according to the invention to cultured nasal cells from PE40 patients will result in an increased amount of wild-type USH2A protein that is detectable on Western blot, and as such will demonstrate that AON-based therapy will not only restore normal splicing of USH2A pseudoexon constructs at least to some extent, but also results in restoring USH2A PE40 mRNA and results in restoring USH2A protein function.

Definitions

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO: 1 containing the nucleic acid sequence coding for the polypeptide should prevail.

All patent and literature references cited in the present specification are hereby incorporated by reference in their entirety.

FIGURE LEGENDS

FIG. 1: Principle of AON-based therapy for USH2A PE40
a) Normal USH2A mRNA splicing of exons 40 and 41, resulting in wild-type USH2A protein.
b) The deep intronic USH-causing mutation is an A-to-G transition (underlined and indicated with an asterisk) in intron 40 of USH2A. This mutation creates a splice donor site, which results in the inclusion of an aberrant exon to the USH2A mRNA and subsequent premature termination of the USH2A protein.
c) Upon binding of sequence-specific AONs, factors involved in splicing will not recognize the aberrant splice donor site in intron 40, resulting in redirection of normal USH2A splicing and synthesis of a correct USH2A protein.

FIG. 2: AON-induced skipping of USH2A PE40
a) RT-PCR analysis of RHO ex3-USH2A PE40 wildtype/mutant-RHO ex5 mRNA's isolated from transfected HEK293T cells that were cultured in the absence or presence of AON1 or AON2 directed against the aberrant USH2A PE40 exon in a final concentration of 1.0 μM. The upper band represents the aberrant RHO-USH2A PE40 splice product, whereas the lower band represents the "corrected" transcript without USH2A PE40. MQ: negative water control.
b) Specificity of AON-based rescue. Similar to A), cells were co-transfected with pCI-neo-RHO ex3-5_USH2A PE40 wildtype/mutant and AON2,or a sense oligonucleotide directed to the same target site (SON2). RT-PCR reaction using primers located in RHO exon 3 and exon 5.

Figure 3A:
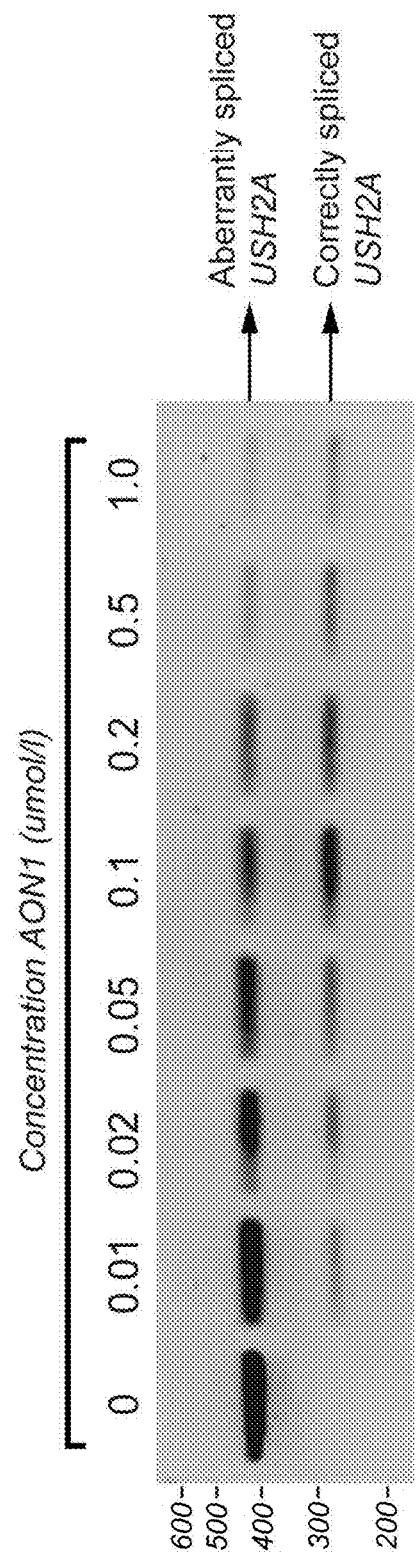
FIG. 3A illustrates RT-PCR analysis of RHO ex3-USH2A PE40 mutant-RHO ex5 mRNA's isolated from transfected HEK293T cells that were cultured in the absence or presence of different total concentrations of AON1 (a)
Figure 3B:
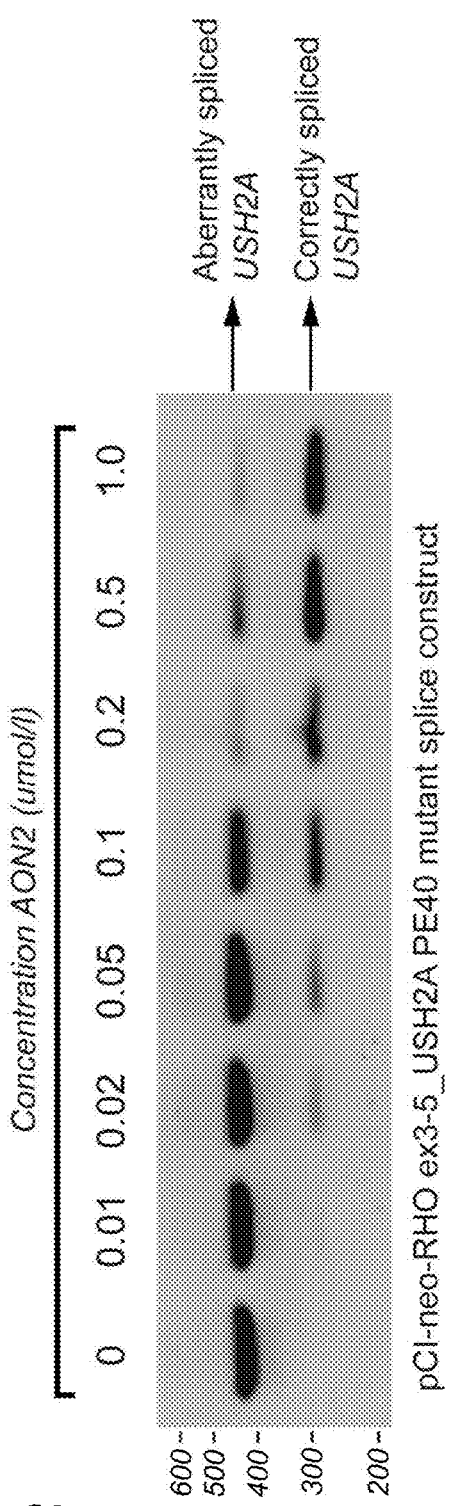
FIG. 3B illustrates RT-PCR analysis of RHO ex3-USH2A PE40 mutant-RHO ex5 mRNA's isolated from transfected HEK293T cells that were cultured in the absence or presence of different total concentrations of AON2 (b).
Figure 3C:
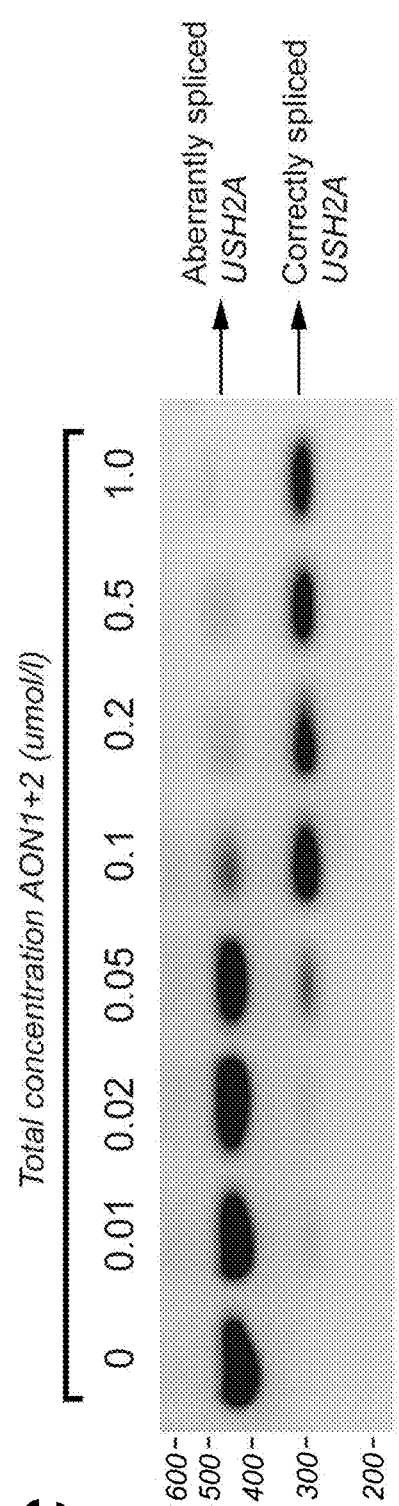
FIG. 3C illustrates RT-PCR analysis of RHO ex3-USH2A PE40 mutant-RHO ex5 mRNA's isolated from transfected HEK293T cells that were cultured in the absence or presence of different total concentrations of AON1+2 (c).

FIG. 3: Titration curves for the AONs directed against USH2A PE40

RT-PCR analysis of RHO ex3-USH2A PE40 mutant-RHO ex5 mRNA's isolated from transfected HEK293T cells that were cultured in the absence or presence of different total concentrations of AON1 (a), AON2 (b) or AON1+2 (c), ranging from 0 to 1.0 µM. Primers were located in RHO exon 3 and exon 5. The upper band represents the aberrant RHO-USH2A PE40 splice product, whereas the lower band represents the "corrected" transcript without USH2A PE40.

FIG. 4: AON-induced skipping of USH2A exon13 and exon50 a) RT-PCR analysis of RHO ex3-USH2A exon13-RHO ex5 mRNA's isolated from transfected HEK293T cells that were cultured in the absence or presence of AON1 or AON2 directed against USH2A exon13 in a final concentration of 1.0 µM. Primers were located in RHO exon 3 and exon 5. The upper band represents the RHO-USH2A exon13 splice product, whereas the lower band represents the "corrected" transcript without USH2A exon13. When applied alone, addition of AON1 or 2 also gives rise to a transcript containing partially skipped exon13. Application of a combination of AON1+2 results in the skipping of complete exon13.

b) Similar to (a), cells were co-transfected with pCI-neo-RHO ex3-5_USH2A exon50 and AON1 or AON2 directed against USH2A exon50 in a final concentration of 1.0 µM. The upper band represents the RHO-USH2A exon50 splice product, whereas the lower band represents the "corrected" transcript without USH2A exon50. AON1 seems not to have major exon skipping potential but enhances the skipping potential of AON2 when applied in combination with AON2.

Figure 5:
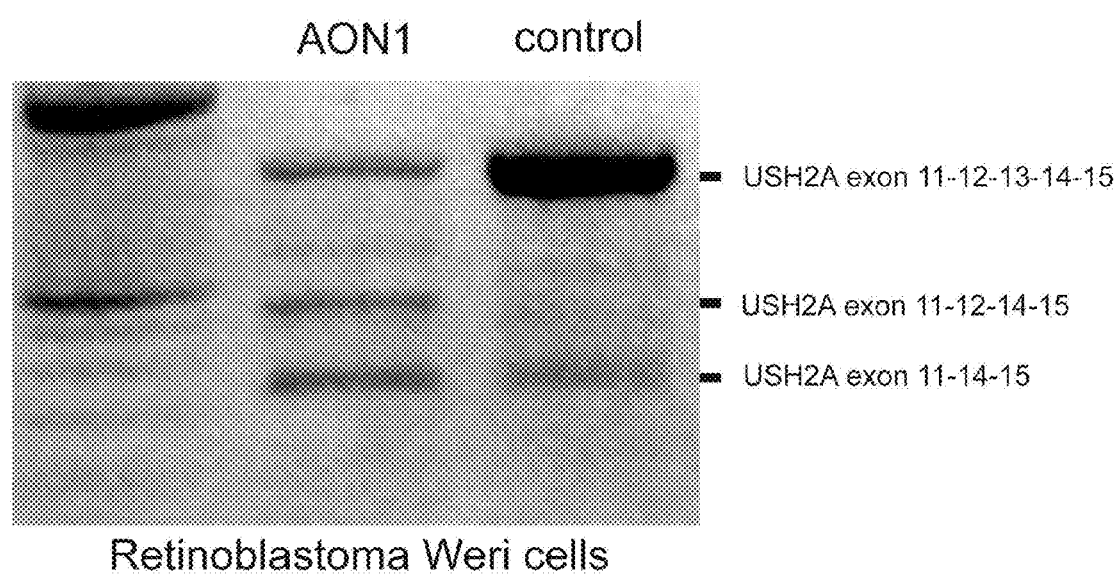
FIG. 5 illustrates RT-PCR analysis of USH2A mRNA isolated from retinoblastoma Weri cells that were cultured in the absence or presence of AON1 directed against USH2A exon13 in a final concentration of 1.0 µM.

FIG. 5: AON-induced skipping of USH2A exon13 in retinoblastoma Weri cells

RT-PCR analysis of USH2A mRNA isolated from retinoblastoma Weri cells that were cultured in the absence or presence of AON1 directed against USH2A exon13 in a final concentration of 1.0 µM. The upper band represents the USH2A wild-type splice product, whereas the lower band represents the transcript lacking USH2A exon12 and 13. Application of AON1 results in the skipping of complete exon13 in approximately 50% of the transcripts.

Figure 6A:
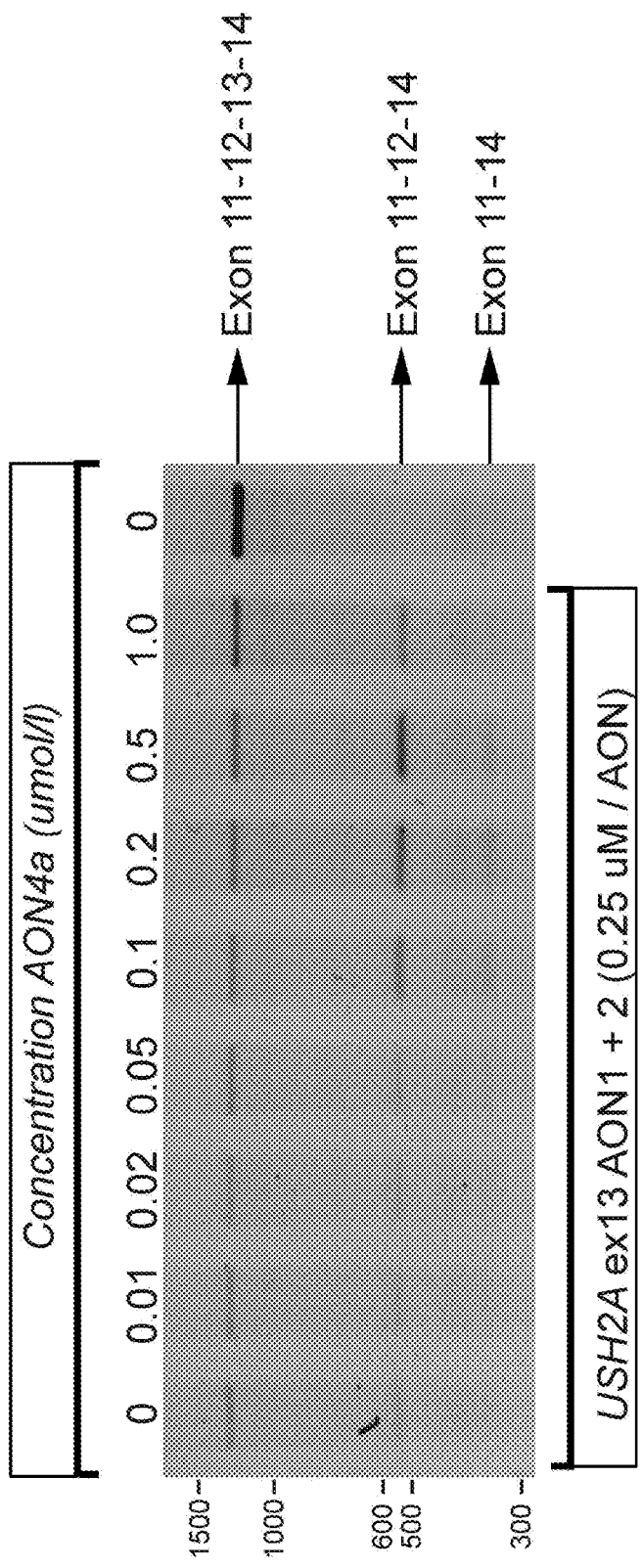
FIG. 6A illustrates RT-PCR analysis of USH2A mRNA isolated from retinoblastoma Weri cells that were cultured in the absence or presence of various concentrations of AON4a (SEQ ID No; 39) directed against intronic splice silencer (ISS) sites in USH2A intron12, combined with AON1+2 (SEQ ID NO: 15 and 16) directed against USH2A exon13 (both at a concentration of 0.25 µM).

FIG. 6A, B: AON-induced retention of USH2A exon12 in retinoblastoma Weri cells

RT-PCR analysis of USH2A mRNA isolated from retinoblastoma Weri cells that were cultured in the absence or presence of various concentrations of AON4a (SEQ ID No; 39) directed against intronic splice silencer (ISS) sites in USH2A intron12, combined with AON1+2 (SEQ ID NO: 15 and 16) directed against USH2A exon13 (both at a concentration of 0.25 µM). The upper band represents the USH2A wild-type splice product, the middle band represents the transcript lacking USH2A exon13, whereas the lower band represents the transcript lacking USH2A exon12 and 13. Application of increasing amounts of AON4a (SEQ ID NO: 39) results in the retention of exon12 in the USH2A transcript (A). Quantification of the exon12 retention was determined by assessing the ratio of the intensity of the wildtype fragment and the fragment lacking exon13 (B). The optimal dose for AON4a (SEQ ID NO: 39) in the current experiment is approximately in between 0.1 and 0.5 µM.

FIG. 7: Skipping of USH2A PE40 by rAAV-based AON delivery

RT-PCR analysis of RHO ex3-USH2A PE40 wildtype/mutant-RHO ex5 mRNA's isolated from transfected HEK293T cells that were cultured in the absence or presence of 1.0 µg pSMD2-U7-USH2A PE40-AON1 (SEQ ID NO: 42) or pSMD2-U7-USH2A PE40-AON2 (SEQ ID NO: 43) directed against the aberrant USH2A PE40 exon. As a negative control, 1.0 µg of the pSMD2-U7-USH2A PE40-SON2 (SEQ ID NO: 44) was transfected. The upper band represents the aberrant RHO-USH2A PE40 splice product, whereas the lower band represents the "corrected" transcript without USH2A PE40.

EXAMPLES

Material and Methods
Design Antisense Oligonucleotides

The sequence of USH2A PE40, exon 13 and exon 50 was analyzed for the presence of exonic splice enhancer motifs (SC35 type) using the ESE finder 3.0 program (http://rulai.cshl.edu/cgibin/tools/ESE3/esefinder.cgi?process=home). RNA antisense oligonucleotides were purchased from Eurogentec, and designed with a Tm of 58° C., and modified with a 2'-O-methyl group at the sugar chain and a phosphothiorate backbone, and dissolved in phosphate buffered saline.

Minigene Splice Constructs

A pCI-NEO-based plasmid containing the genomic region encompassing exons 3-5 of RHO was used to test the efficiency of the used AONs in in vitro splicing assays (Gamundi et al, 2008). For this purpose RHO exon4 and part of the flanking intronic sequences is replaced by human USH2A exon13, exon50 or pseudoexon40 (PE40) together with 500 bp of 5' and 3' flanking intronic sequence using Gateway cloning technology (Invitrogen).

Cell Culture

HEK293T cells were cultured in DMEM medium (Gibco) containing 10% (v/v) fetal calf serum (Sigma), 1% 10 U/µl penicillin and 10 µg/µl streptomycin (Gibco), at a density of $0.5 \times 10^6$ cells/ml. Cells were passaged twice a week. Human retinoblastoma cells (Rb-Weri) were cultured in RPMI1640 medium (Gibco) containing 10% (v/v) fetal calf serum (Sigma), 1% 10 U/µl penicillin and 10 µg/µl streptomycin (Gibco), and 1% GlutaMAX (Gibco), at a density of $0.5 \times 10^6$ cells/ml. Cells were passaged twice a week.

Transfection of AONs in Retinoblastoma Weri Cells

Prior to transfection, $1.0 \times 10^6$ cells were seeded in each well of a 6-wells plate, in a total volume of 0.9 ml Optimem. Transfection mixtures were prepared by combining 50 µl Optimem supplemented with 1 µl AON in a desired concentration and 50 µl Optimem supplemented with 1.25 µl Lipofectamine 2000 (Invitrogen). Incubate both mixtures for 5' at room temperature. After this incubation step add both mixtures together, mix well and incubate for another 20' at room temperature, before addition to the cells. Forty-eight hours after transfection, cells were collected and washed with 1×PBS, before directly proceeding to RNA isolation.

Co-Transfection of AONs and Minigene Splice Constructs in HEK293T Cells

A day before transfection, $1.0 \times 10^6$ cells were seeded in each well of a 6-wells plate, in a total volume of 0.9 ml complete medium. Transfection mixtures were prepared by combining 1 µl AON in a desired concentration, 9 µl (=500 ng) of plasmid DNA and 90 µl transfection reagent (PEI), and incubated at room temperature for 10 minutes, before addition to the cells. Forty-eight hours after transfection, cells were collected and washed with 1×PBS, before directly proceeding to RNA isolation.

Generation of pSMD2-U7 snRNA Plasmids

By adopting the method of fusion PCR, USH2A PE40 AON1, AON2 and SON2 were cloned into the pSMD2-U7 snRNA vector. In short, for obtaining the left fragment the AAV-XbaI forward primer (SEQ ID NO: 45) was combined with the U7-AON1/2/SON2 reverse primer (SEQ ID NO:'s 47, 49 and 51, respectively) and for obtaining the right fragment the U7-AON1/2/SON2 forward primer (SEQ ID NO:'s 48, 50 and 52, respectively) was combined with the AAV-NheI reverse primer (SEQ ID NO: 46) using the empty pSMD2-U7 snRNA vector as a template. In a second PCR both fragments are fused together and amplified using the AAV-XbaI forward primer (SEQ ID NO: 45) and the AAV-NheI reverse primer (SEQ ID NO: 47). The resulting fragment and the empty pSMD2-U7 snRNA vector were subsequently digested with XbaI and NheI, after which the digested fragment was ligated into the pSMD2-U7 snRNA vector. The resulting plasmids (pSMD2(AAV) U7snRNA_hUSH2A PE40 AON1 (SEQ ID NO: 42), pSMD2(AAV)U7snRNA_hUSH2A PE40 AON2 (SEQ ID NO: 43 and pSMD2(AAV)U7snRNA_hUSH2A PE40 SON2 (SEQ ID NO: 44)) were sequence verified.

Co-Transfection of pSMD2-AON and Minigene Splice Constructs in HEK293T Cells

A day before transfection, $1.0 \times 10^6$ cells were seeded in each well of a 6-wells plate, in a total volume of 0.9 ml complete medium. Transfection mixtures were prepared by combining 1 µg of pSMD2-AON plasmid DNA, 1 µg of USH2A PE40 minigene splice construct DNA and 90 µl transfection reagent (PEI), and incubated at room temperature for 10 minutes, before addition to the cells. Forty-eight hours after transfection, cells were collected and washed with 1×PBS, before directly proceeding to RNA isolation.

RNA Isolation and RT-PCR

Total RNA was isolated from transfected HEK293T or retinoblastoma Weri cells using the Nucleospin RNA II isolation kit (Machery Nagel), according to manufacturer's protocol. Subsequently, 1 µg of total RNA was used for cDNA synthesis using the iScript cDNA synthesis kit (Bio-Rad). Five percent of the cDNA was used for each PCR reaction. For the minigene splice assays, part of the cDNA was amplified under standard PCR conditions, and using forward primer 5'-cggaggtcaacaacgagtct-3' (SEQ ID NO: 34) and reverse primer 5'-aggtgtagggatgggagac-3' (SEQ ID NO: 35) that are located in exon 3 and exon 5 of the human RHO gene, respectively. For the Rb-Weri exon skipping experiments, part of the USH2A cDNA was amplified under standard PCR conditions using forward primer 5'-aagttggt-gcagatccttcg-3' (SEQ ID NO: 36) and reverse primer 5'-agaaacactggcctgtgacc-3' (SEQ ID NO: 37) that are located in exon 11 and exon 15 of the human USH2A gene, respectively. PCR products were resolved on a 1.5% agarose gel. Bands presumably representing correctly and aberrantly spliced USH2A were excised from the gel, purified using Nucleospin Extract II isolation kit and sequenced from both strands with the ABIPRISM Big Dye Terminator Cycle Sequencing V2.0 Ready Reaction kit and the ABIPRISM 3730 DNA analyzer (Applied Biosystems).

Results

The intronic USH2A mutation (c.7595-2144A>G) creates a cryptic splice donor site that results in the inclusion of an aberrant exon (PE40) into the USH2A mRNA (FIG. 1A,B). Addition of AONs directed against the aberrant exon would prevent the insertion of this exon by preventing the binding of factors that are essential for splicing such as the U1- and U2 snRNP complexes, and serine-arginine rich proteins, thereby restoring normal USH2A splicing and protein synthesis (FIG. 1C). AONs can target splice sites as well as exonic sequences, although in the particular case of the Duchenne muscular dystrophy (DMD) gene, AONs targeting exonic regions tend to outperform those that target the splice sites (Aartsma-Rus et al, 2010). In addition, previous studies have suggested a positive correlation between the capability of AONs to induce exon skipping and the presence of predicted SC35 splice factor binding sites in the target sequence (Aartsma-Rus et al, 2008). To design an AON with high exon-skipping potential, the aberrant USH2A exon (152 nucleotides exonic sequence plus 15 nucleotides of intronic sequence on each side) was scrutinized for exonic splice enhancer binding motifs, using the ESE finder 3.0 program (Smith et al, 2006). Within the aberrant exon, two regions with respectively three and two SC35-binding motifs were predicted (data not shown). Hence, two AONs were designed such that it encompassed these regions with SC35 motifs (designated AON1, SEQ ID NO: 10; and AON2, SEQ ID NO: 11), and being complementary to the USH2A mRNA. To determine whether AONs 1 and 2 have exon-skipping potential in vitro, HEK293T cells transfected with a pCI-neo based minigene containing the genomic region encompassing RHO exon 3-USH2A PE40 wild-type/mutant-RHO exons were cultured in the presence or absence of 1 µM AON1 and AON2. As expected in the wild-type situation, PE40 is not incorporated in the transcript. In the mutant situation, PE40 is recognized as an exon and therefore incorporated in the transcript. Upon addition of either AON1, or AON2, a strong decrease in aberrantly spliced transcripts was noted (FIG. 2, upper panel). In this condition, AON2 appeared to be the most potent AON. Next, the specificity of AON2 was assessed by transfecting a sense oligonucleotide directed to the same target site (SON2, SEQ ID NO: 25). RT-PCR analysis performed after the minigene splice assay showed that in the cells transfected with SON2, only the aberrantly spliced RHO-USH2A PE40 mRNA molecules are still present (FIG. 2, lower panel), demonstrating the specificity of the antisense sequence. Interestingly, the decrease in aberrantly spliced transcripts appears to coincide with an increased intensity of the product representing correctly spliced mRNA. These data indicate that the aberrant product is not degraded, but that the AON transfection truly induces exon skipping, eventually resulting in the synthesis of more correctly spliced wild-type USH2A mRNA.

To determine the effective dose of AON1 and 2 in minigene splice assays, cells were co-transfected with various concentrations of AON1, 2 and 1+2, ranging from a total concentration of 0.01 to 1.0 µM. Even at the lowest concentration of 0.01 µM, a marked reduction in aberrantly spliced USH2A was observed for AON1 (FIG. 3). A maximum amount of exon skipping was still observed at 0.1 µM of AON, indicating that this concentrations is sufficient to convert more than half of the aberrantly spliced USH2A (FIG. 3).

Next we evaluated the USH2A PE40 skipping potential of AONs 1 and 2 when delivered using an AAV-based delivery method. For this purpose the AON1, 2 and SON2 sequences were cloned in the pSMD2-U7 snRNA plasmid, targeting the expression of AONs directly to the spliceosome. HEK293T cells were transfected with a mixture containing 1 µg of pSMD2-AON plasmid DNA and 1 µg of USH2A PE40 minigene splice construct DNA. Forty-eight hours after transfection, cells were collected and washed with 1×PBS, before directly proceeding to RNA isolation. Upon addition of either pSMD2-U7 snRNA-AON1 or -AON2, a strong decrease in aberrantly spliced transcripts was noted (FIG. 7). In this condition, AON1 appeared to be the most potent AON, in contrast to the naked AONs delivery.

RT-PCR analysis performed after co-transfection of pSMD2-U7 snRNA-SON2 with the USH2A PE40 minigene splice construct showed that only the aberrantly spliced RHO-USH2A PE40 mRNA molecules are still present (FIG. 7), demonstrating the specificity of the antisense sequence. AAV-based delivery of AONs capable of redirecting USH2A PE40 splicing appears to be potent as well.

Figure 4A:
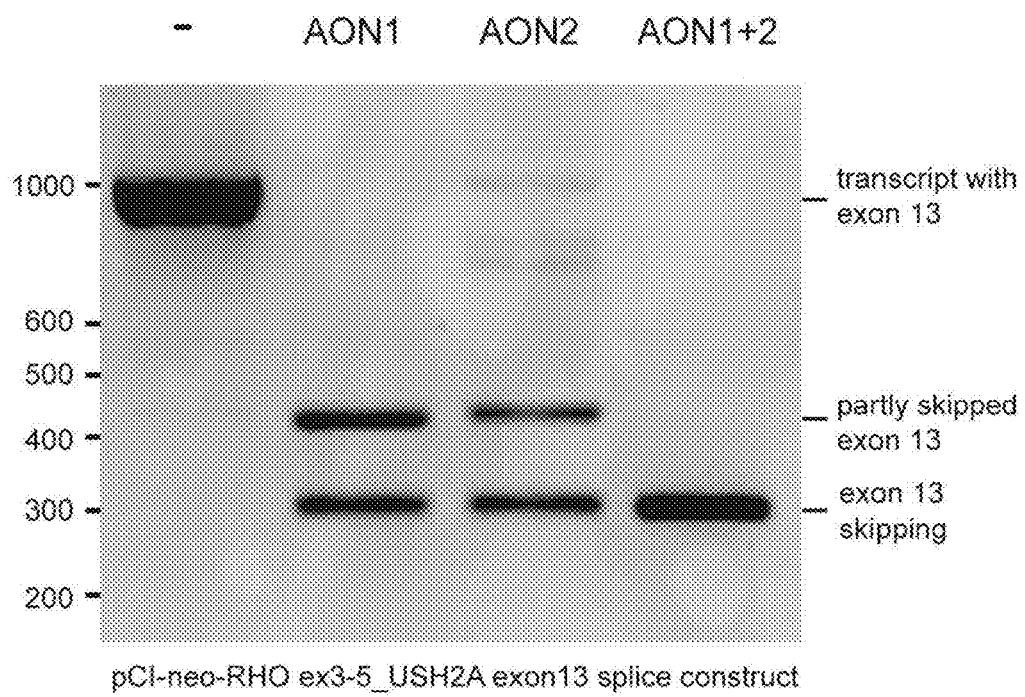
FIG. 4A illustrates RT-PCR analysis of RHO ex3-USH2A exon13-RHO ex5 mRNA's isolated from transfected HEK293T cells that were cultured in the absence or presence of AON1 or AON2 directed against USH2A exon13 in a final concentration of 1.0 µM.
Figure 4B:
FIG. 4B illustrates RT-PCR similar to (a), cells were co-transfected with pCI-neo-RHO ex3-5_USH2A exon50 and AON1 or AON2 directed against USH2A exon50 in a final concentration of 1.0 µM.

Another way to use AON-treatment is to skip exons that carry (protein-truncating) mutations in such a way, that the reading frame of the mRNA remains intact and a (partially) functional protein is made. Two frequently mutated exons in the USH2A gene that fulfill the criteria for exon skipping are exon 13 and exon 50 (Table 2 and 3). For both exons we designed two AONs using the settings described above. In vitro splicing assays were performed using a pCI-neo based minigene that contained, besides the genomic region around RHO exon3-5, USH2A exon 13 or exon 50 surrounded by 500 bp of intronic sequence. During these minigene splice assays HEK293T cells were co-transfected with a final concentration of 1.0 µM AON1, AON2 or AON1+2. Addition of AON1 (SEQ ID NO: 15) and AON2 (SEQ ID NO: 16) directed against two different regions containing SC35 motifs in USH2A exon13 resulted in the partial or complete skipping of exon13. Combination of AONs 1+2 resulted in the complete skipping of exon13 in nearly 100% of the transcripts (FIG. 4A). A similar assay using AON1 (SEQ ID NO: 17) and AON2 (SEQ ID NO: 18) directed against USH2A exon 50 was performed. Interestingly, AON2 resulted in relatively low levels of exon skipping. In contrast, AON1 hardly showed any exon skipping potential (FIG. 4B). These data demonstrate the sequence specificity in AON-based exon skipping of USH2A exon 50. Supplementing AON2 with AON1 increased the skipping potential of the former (FIG. 4B).

Finally, RT-PCR analysis revealed the expression of USH2A in retinoblastoma Weri cells (FIG. 5). Using a forward primer located in exon 11 and a reverse primer in exon 15 we identified a naturally occurring combined skipping of exon 12 and 13. Culturing retinoblastoma Weri cells in the presence of 1.0 µM AON1 (SEQ ID NO: 15) directed against USH2A exon 13 resulted in the skipping of exon 13 in approximately 50% of the transcripts, indicative for a possible therapeutic potential.

Figure 6B:
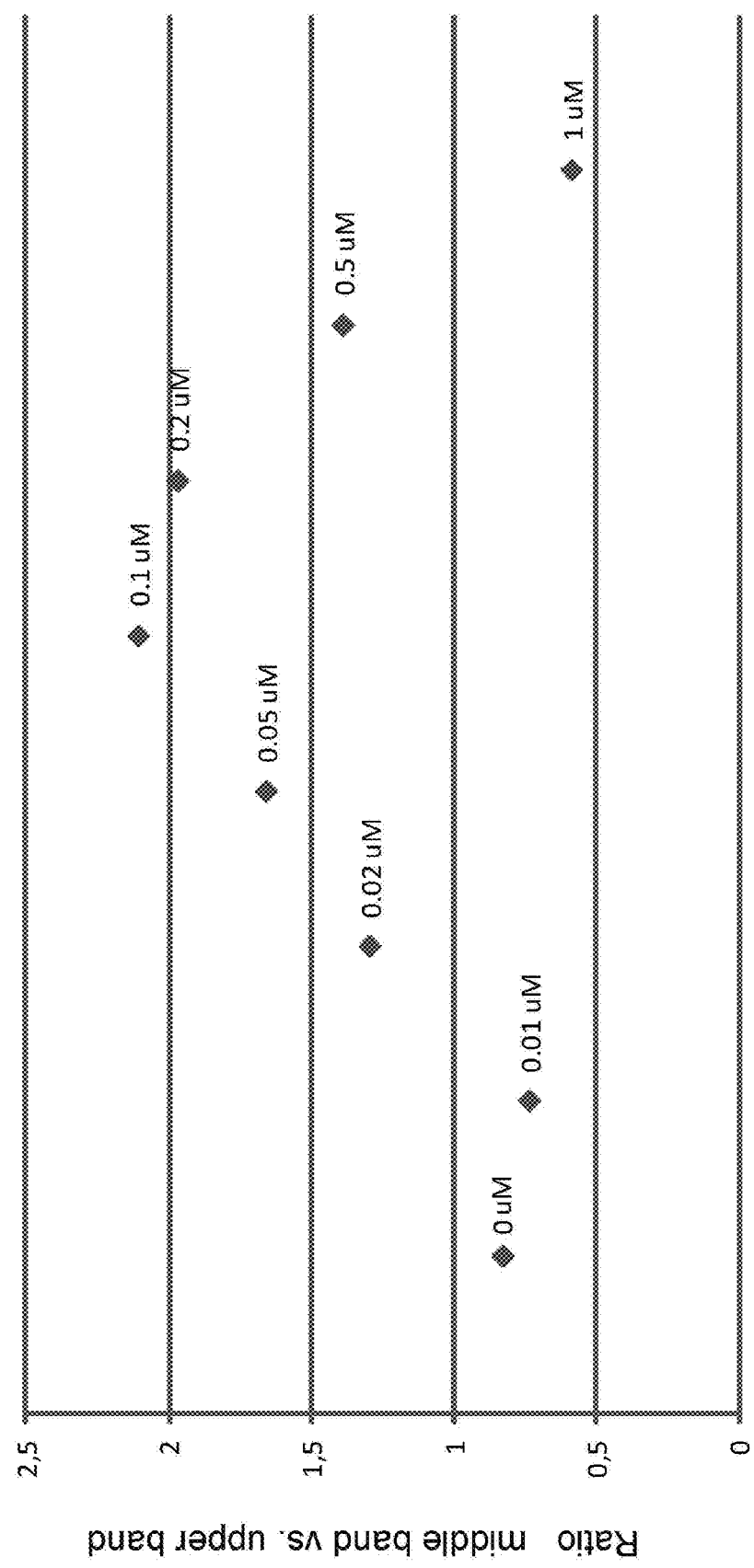
FIG. 6B illustrates quantification of the exon12 retention was determined by assessing the ratio of the intensity of the wildtype fragment and the fragment lacking exon13. The optimal dose for AON4a (SEQ ID NO: 39) in the current experiment is approximately in between 0.1 and 0.5 µM.

In order to prevent the AON-induced skipping of exon12, we designed AON4a (SEQ ID NO: 39) directed against intronic splice silencer sites (ISS) in intron 12 and evaluated its effect in retinoblastoma Weri cells. For this, a combination of 0.25 µM AON1 (SEQ ID NO: 15), 0.25 µM AON2 (SEQ ID NO: 16) and various amounts of AON4a (ranging from 0-1.0 µM; FIG. 6B) were transfected. RT-PCR analysis analysis and subsequent quantification of the results revealed that application of increasing amounts of AON4a results in the retention of exon 12 in the USH2A transcript (FIG. 6A). Quantification of the exon 12 retention was performed by assessing the ratio of the intensity of the wildtype fragment and the fragment lacking exon 13 (FIG. 6B). The optimal dose for AON4a in the current experiment was approximately in between 0.1 and 0.5 µM. A combination of AONs 1, 2 and 4a is therefore quite effective.

TABLE 1

Sequences

| SEQ ID NO: | Name: |
|---|---|
| 1 | Wild-type USH2A coding DNA |
| 2 | PE40 USH2A coding DNA |
| 3 | Wild-type USH2A protein |
| 4 | PE40 USH2A protein (putative) |
| 5 | pseudoexon coding DNA |
| 6 | pseudoexon protein sequence |
| 7 | intron 40 genomic DNA |
| 8 | USH2A genomic DNA wild-type |
| 9 | USH2A genomic DNA PE40 |
| 10 | AON1-PE40 |
| 11 | AON2-PE40 |
| 12 | pseudoexon 40 and flanking sequences DNA |
| 13 | exon 13 and flanking sequences DNA |
| 14 | exon 50 and flanking sequences DNA |
| 15 | AON1-exon13 |
| 16 | AON2-exon13 |
| 17 | AON1-exon50 |
| 18 | AON2-exon50 |
| 19 | AON1-PE40 target site and flanking sequences (+10 nt) |
| 20 | AON2-PE40 target site and flanking sequences (+10 nt) |
| 21 | AON1-exon13 target site and flanking sequences (+10 nt) |
| 22 | AON2-exon13 target site and flanking sequences (+10 nt) |
| 23 | AON1-exon50 target site and flanking sequences (+10 nt) |
| 24 | AON2-exon50 target site and flanking sequences (+10 nt) |
| 25 | SON2-PE40 |
| 26 | AON1-PE40 target site and flanking sequences (+5 nt) |
| 27 | AON2-PE40 target site and flanking sequences (+5 nt) |
| 28 | AON1-exon13 target site and flanking sequences (+5 nt) |
| 29 | AON2-exon13 target site and flanking sequences (+5 nt) |
| 30 | AON1-exon50 target site and flanking sequences (+5 nt) |
| 31 | AON2-exon50 target site and flanking sequences (+5 nt) |
| 32 | exon 13 DNA sequence |
| 33 | exon 50 DNA sequence |
| 34 | Rho exon 3 FW PCR primer |
| 35 | Rho exon 5 REV PCR primer |
| 36 | USH2A exon 11 FW PCR primer |
| 37 | USH2A exon 14 REV PCR primer |
| 38 | Wild-type USH2A Exon 11-Exon 13 genomic DNA |
| 39 | AON4a-exon 12 |
| 40 | AON4a-exon 12 target site and flanking sequences (+10 nt) |
| 41 | AON4a-exon 12 target site and flanking sequences (+5 nt) |
| 42 | pSMD2(AAV)U7snRNA_hUSH2A PE40 AON1 |
| 43 | pSMD2(AAV)U7snRNA_hUSH2A PE40 AON2 |
| 44 | pSMD2(AAV)U7snRNA_hUSH2A PE40 SON2 |
| 45 | AAV XbaI FW PCR primer |
| 46 | AAV NheI REV PCR primer |
| 47 | U7 + AON1 REV PCR primer |
| 48 | U7 + AON1 FW PCR primer |
| 49 | U7 + AON2 REV PCR primer |
| 50 | U7 + AON2 FW PCR primer |
| 51 | U7 + SON2 REV PCR primer |
| 52 | U7 + SON2 FW PCR primer |

REFERENCES

Lentz et al., Nat Med. 2013 March; 19(3):345-50. doi: 10.1038/nm.3106. Epub 2013 Feb. 4.

Vaché et al., Hum Mutat. 2012 January; 33(1):104-8. doi: 10.1002/humu.21634. Epub 2011 Nov. 16.

Friesen and Darby, Nature Structural Biology 5: 543-546 (1998).

Dorn and Kippenberger, Curr Opin Mol Ther 2008 10(1) 10-20.

Nielsen, et al. (1991)Science 254, 1497-1500.

Govindaraju and Kumar (2005) Chem. Commun, 495-497.

Egholm et al (1993)Nature 365, 566-568.

Morita et al. 2001. Nucleic Acid Res Supplement No. 1: 241-242.

Gorman L, et al, Stable alteration of pre-mRNA splicing patterns by modified U7 small nuclear RNAs. Proc Natl Acad Sci USA 1998; 95(9):4929-34.

Suter D, et al, Double-target antisense U7 snRNAs promote efficient skipping of an aberrant exon in three human beta-thalassemic mutations. Hum Mol Genet 1999; 8(13): 2415-23.

Remington: The Science and Practice of Pharmacy, 20th Edition. Baltimore, Md.: Lippincott Williams k Wilkins, 2000.

Kimberling W J, Hildebrand M S, Shearer A E, Jensen M L, Halder J A, Trzupek K, Cohn E S, Weleber R G, Stone E M, Smith R J. Frequency of Usher syndrome in two pediatric populations: implications for genetic screening of deaf and hard of hearing children (2010) Genet Med 12:512-516.

Hartong D T, Berson E L, Dryja T P. Retinitis pigmentosa (2006) Lancet, 368(9549): 1795-1809.

McGee T L, Seyedahmadi B J, Sweeney M O et al, Novel mutations in the long isoform of the USH2A gene in patients with Usher syndrome type II or nonsyndromic retinitis pigmentosa (2010) J. Med. Genet., 47(7):499-506.

Vaché C, Besnard T, le Berre P, García-Garcia G, Baux D, Larrieu L, Abadie C, Blanchet C, Bolz H J, Millan J, Hamel C, Malcolm S, Claustres M, Roux A F. Usher syndrome type 2 caused by activation of an USH2A pseudoexon: implications for diagnosis and therapy. Human Mutation (2012) 33(1):104-8.

Bainbridge, J. W., Smith, A. J., Barker, S. S., Robbie, S., Henderson, R., Balaggan, K., Viswanathan, A., Holder, G. E., Stockman, A., Tyler, N. et al (2008). Effect of gene therapy on visual function in Leber's congenital amaurosis. N Engl J Med 358, 2231-2239.

Cideciyan, A. V., Aleman, T. S., Boye, S. L., Schwartz, S. B., Kaushal, S., Roman, A. J., Pang, J. J., Sumaroka, A., Windsor, E. A., Wilson, J. M. et al (2008). Human gene therapy for RPE65 isomerase deficiency activates the retinoid cycle of vision but with slow rod kinetics. Proc Natl Acad Sci USA 105, 15112-15117.

Hauswirth, W., Aleman, T. S., Kaushal, S., Cideciyan, A. V., Schwartz, S. B., Wang, L., Conlon, T., Boye, S. L., Flotte, T. R., Byrne, B. et al (2008). Phase I Trial of Leber Congenital Amaurosis due to Estrada-Mutations by Ocular Subretinal Injection of Adeno-Associated Virus Gene Vector: Short-Term Results. Hum Gene Ther Maguire, A. M., Simonelli, F., Pierce, E. A., Pugh, E. N., Jr., Mingozzi, F., Bennicelli, J., Banfi, S., Marshall, K. A., Testa, F., Surace, E. M. et al (2008). Safety and efficacy of gene transfer for Leber's congenital amaurosis. N Engl J Med 358, 2240-2248.

Hashimoto T, Gibbs D, Lillo C, Azarian S M, Legacki E, Zhang X M, Yang X J, Williams D S. Lentiviral gene replacement therapy of retinas in a mouse model for Usher syndrome type 1B (2007) Gene Ther. 14(7):584-94.

Lopes V S, Boye S E, Louie C M, Boye S, Dyka F, Chiodo V, Fofo H, Hauswirth W W, Williams D S. Retinal gene therapy with a large MYO7A cDNA using adeno-associated virus (2013) Gene Ther. 20(8):824-33.

Colella P, Trapani I, Cesi G, Sommella A, Manfredi A, Puppo A, Iodice C, Rossi S, Simonelli F, Giunti M, Bacci M L, Auricchio A. Efficient gene delivery to the cone-enriched pig retina by dual AAV vectors (2014) Gene Ther. 21(4):450-6.

Zallocchi M, Binley K, Lad Y, Ellis S, Widdowson P, Iqball S, Scripps V, Kelleher M, Loader J, Miskin J, Peng Y W, Wang W M, Cheung L, Delimont D, Mitrophanous K A, Cosgrove D. EIAV-based retinal gene therapy in the shaker 1 mouse model for usher syndrome type 1B: development of UshStat (2014) PLoS One 9(4):e94272.

Scaffidi P, Misteli T, Reversal of the cellular phenotype in the premature aging disease Hutchinson-Gilford progeria syndrome (2005) Nat. Med., 11(4):440-445.

Cirak S, Feng L, Anthony K et al, Restoration of the Dystrophin-associated Glycoprotein Complex After Exon Skipping Therapy in Duchenne Muscular Dystrophy (2011) Mol. Ther., Cirak S, rechavala-Gomeza V, Guglieri M et al, Exon skipping and dystrophin restoration in patients with Duchenne muscular dystrophy after systemic phosphorodiamidate morpholino oligomer treatment: an open-label, phase 2, dose-escalation study (2011) Lancet, 378 (9791):595-605.

Goemans N M, Tulinius M, van den Akker J T et al, Systemic administration of PRO051 in Duchenne's muscular dystrophy (2011) N. Engl. J. Med., 364(16):1513-1522.

Gamundi M J, Hernan I, Muntanyola M et al, Transcriptional expression of cis-acting and trans-acting splicing mutations cause autosomal dominant retinitis pigmentosa (2008) Hum. Mutat., 29(6):869-878.

Aartsma-Rus, A., Houlleberghs, H., van Deutekom, J. C., van Ommen, G. J., and 't Hoen, P. A. Exonic sequences provide better targets for antisense oligonucleotides than splice site sequences in the modulation of Duchenne muscular dystrophy splicing (2010) Oligonucleotides 20, 69-77.

Aartsma-Rus, A., van, V. L., Hirschi, M., Janson, A. A., Heemskerk, H., de Winter, C. L., de, K. S., van Deutekom, J. C., 't Hoen, P. A., and van Ommen, G. J. Guidelines for Antisense Oligonucleotide Design and Insight Into Splice-modulating Mechanisms (2008) Mol Ther.

Smith, P. J., Zhang, C., Wang, J., Chew, S. L., Zhang, M. Q., and Krainer, A. R. An increased specificity score matrix for the prediction of SF2/ASF specific exonic splicing enhancers (2006) Hum Mol Genet 15, 2490-2508.

Garcia-Garcia G, Aparisi M J, Jaijo T, Rodrigo R, Leon A M, Avila-Fernandez A, Blanco-Kelly F, Bernal S, Navarro R, Diaz-Llopis M, Baiget M, Ayuso C, Millan J M, Aller E. Mutational screening of the USH2A gene in Spanish USH patients reveals 23 novel pathogenic mutations. (2011) Orphanet J Rare Dis. 6:65

Dreyer B, Brox V, Tranebjaerg L, Rosenberg T, Sadeghi A M, Möller C, Nilssen O. Spectrum of USH2A mutations in Scandinavian patients with Usher syndrome type II. (2008) Hum Mutat. 29(3):451.

McGee T L, Seyedahmadi B J, Sweeney M O, Dryja T P, Berson E L. Novel mutations in the long isoform of the USH2A gene in patients with Usher syndrome type II or non-syndromic retinitis pigmentosa. (2010) J Med Genet. 47(7):499-506.

Le Quesne Stabej P, Saihan Z, Rangesh N, Steele-Stallard H B, Ambrose J, Coffey A, Emmerson J, Haralambous E, Hughes Y, Steel K P, Luxon L M, Webster A R, Bitner-Glindzicz M. Comprehensive sequence analysis of nine Usher syndrome genes in the UK National Collaborative Usher Study. (2012) J Med Genet. 49(1):27-36.

Baux D, Larrieu L, Blanchet C, Hamel C, Ben Salah S, Vielle A, Gilbert-Dussardier B, Holder M, Calvas P, Philip N, Edery P, Bonneau D, Claustres M, Malcolm S, Roux A F. Molecular and in silico analyses of the full-length isoform of usherin identify new pathogenic alleles in Usher type II patients. (2007) Hum Mutat. 28(8):781-9.

Baux D, Blanchet C, Hamel C, Meunier I, Larrieu L, Faugère V, Vaché C, Castorina P, Puech B, Bonneau D, Malcolm S, Claustres M, Roux A F. Enrichment of LOVD-USHbases with 152 USH2A genotypes defines an extensive mutational spectrum and highlights missense hotspots (2014) Hum Mutat. June 18.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10745699B2). An electronic copy of the "Sequence Listing" will also be available from the USPTO upon request and payment of the fee set forth in 37 CFR 1.19(b)(3).

What is claimed is:

1. A single-stranded exon skipping antisense oligonucleotide or a single-stranded exon 12 retention antisense oligonucleotide that is at least 90% complementary to a polynucleotide with the nucleotide sequence selected from the group consisting of SEQ ID NO: 12, 13, and 14, wherein the antisense oligonucleotide has a length of 12 to 30 nucleotides, wherein the antisense oligonucleotide comprises a 2'-O-methoxyethyl modified ribose, a 2'-O-alkyl modified ribose, and/or substituted derivatives of these modifications.

2. The single-stranded exon skipping antisense oligonucleotide or a single-stranded exon 12 retention antisense oligonucleotide according to claim 1, wherein the complementarity to the polynucleotide sequence is at least 90%, 95%, 98% or 99% of the length of the oligonucleotide.

3. The single-stranded exon skipping antisense oligonucleotide or a single-stranded exon 12 retention antisense oligonucleotide according to claim 1, wherein the complementarity to the polynucleotide sequence is 100% of the length of the oligonucleotide.

4. The single-stranded exon skipping antisense oligonucleotide or a single-stranded exon 12 retention antisense oligonucleotide according to claim 1, wherein the oligonucleotide has a length of 20 to 24 nucleotides.

5. The single-stranded exon skipping antisense oligonucleotide or a single-stranded exon 12 retention antisense oligonucleotide according to claim 4, wherein the oligonucleotide comprises or consists of a sequence selected from the group consisting of SEQ ID NO: 10, 11, 15, 16, 17, 18 and 39.

6. A set of oligonucleotides comprising at least two single-stranded exon skipping and/or exon 12 retention antisense oligonucleotides as defined in claim 1.

7. A viral vector expressing a single-stranded exon skipping oligonucleotide or a single-stranded exon 12 retention antisense oligonucleotide that is at 90% complementary to a polynucleotide with the nucleotide sequence selected from the group consisting of SEQ ID NO: 12, 13, and 14, wherein the antisense oligonucleotide has a length of 12 to 30 nucleotides.

8. The viral vector according to claim 7, wherein the complementarity of the oligonucleotide to the polynucleotide sequence is at least 90%, 95%, 98% or 99% of the length of the oligonucleotide.

9. The viral vector according to claim 7, wherein the complementarity of the oligonucleotide to the polynucleotide sequence is 100% of the length of the oligonucleotide.

10. The viral vector according to claim 7, wherein the oligonucleotide has a length of 20 to 24 nucleotides.

11. A pharmaceutical composition comprising a single-stranded exon skipping antisense oligonucleotide or a single-stranded exon 12 retention antisense oligonucleotide according to claim 1, and a pharmaceutically acceptable excipient.

12. A pharmaceutical composition according to claim 11, wherein the pharmaceutical composition is for intravitreal administration and is dosed in an amount ranged from 0.05 mg and 5 mg of total oligonucleotide per eye.

13. A pharmaceutical composition according to claim 11, wherein the pharmaceutical composition is for intravitreal administration and is dosed in an amount ranged from 0.1 and 1 mg of total oligonucleotide per eye.

14. The single-stranded exon skipping antisense oligonucleotide or the single-stranded exon 12 retention antisense oligonucleotide according to claim 1 comprising a 2'-O-alkyl modified ribose, wherein said 2'-O-alkyl modified ribose is a 2'-O-methyl modified ribose, a 2'-O-ethyl modified ribose or a 2'-O-propyl modified ribose.

15. The single-stranded exon skipping antisense oligonucleotide or the single-stranded exon 12 retention antisense oligonucleotide according to claim 1 comprising a substituted derivative of a 2'-O-methoxyethyl modified ribose and/or a 2'-O-alkyl modified ribose, wherein said substituted derivative is a halogenated derivative.

16. The single-stranded exon skipping antisense oligonucleotide or a single-stranded exon 12 retention antisense oligonucleotide of claim 1, wherein the complementarity to the polynucleotide sequence is 100% of the length of the oligonucleotide and wherein the antisense oligonucleotide comprises a 2'-O-methoxyethyl modified ribose, a 2'-O-methyl modified ribose, a 2'-O-ethyl modified ribose or a 2'-O-propyl modified ribose.

17. A pharmaceutical composition comprising a single-stranded exon skipping antisense oligonucleotide or a single-stranded exon 12 retention antisense oligonucleotide according to claim 16, and a pharmaceutically acceptable excipient.

18. A pharmaceutical composition according to claim 17, wherein the pharmaceutical composition is for intravitreal administration and is dosed in an amount ranged from 0.05 mg and 5 mg of total oligonucleotide per eye.

19. The single-stranded exon skipping antisense oligonucleotide or a single-stranded exon 12 retention antisense oligonucleotide of claim 1 that is 100% complementary to a polynucleotide with the nucleotide sequence of SEQ ID NO: 12.

20. The single-stranded exon skipping antisense oligonucleotide or a single-stranded exon 12 retention antisense oligonucleotide of claim 1 that is 100% complementary to a polynucleotide with the nucleotide sequence of SEQ ID NO: 13.

21. The single-stranded exon skipping antisense oligonucleotide or a single-stranded exon 12 retention antisense oligonucleotide of claim 1 that is 100% complementary to a polynucleotide with the nucleotide sequence of SEQ ID NO: 14.

22. The viral vector of claim 7, wherein the single-stranded exon skipping oligonucleotide or a single-stranded exon 12 retention antisense oligonucleotide is 100% complementary to a polynucleotide with the nucleotide of SEQ ID NO: 12.

23. The viral vector of claim 7, wherein the single-stranded exon skipping oligonucleotide or a single-stranded exon 12 retention antisense oligonucleotide is 100% complementary to a polynucleotide with the nucleotide of SEQ ID NO: 13.

24. The viral vector of claim 7, wherein the single-stranded exon skipping oligonucleotide or a single-stranded exon 12 retention antisense oligonucleotide is 100% complementary to a polynucleotide with the nucleotide of SEQ ID NO: 14.

* * * * *